(12) United States Patent
Liechti

(10) Patent No.: US 11,963,946 B2
(45) Date of Patent: *Apr. 23, 2024

(54) MDMA TREATMENT TO ENHANCE ACUTE EMOTIONAL EFFECTS PROFILE OF LSD, PSILOCYBIN, OR OTHER PSYCHEDELICS

(71) Applicant: Universitätsspital Basel, Basel (CH)

(72) Inventor: Matthias Emanuel Liechti, Oberwil (CH)

(73) Assignee: Universitätsspital Basel, Basel (CH)

( * ) Notice: Subject to any disclaimer, the term of this patent is extended or adjusted under 35 U.S.C. 154(b) by 22 days.

This patent is subject to a terminal disclaimer.

(21) Appl. No.: 17/238,088

(22) Filed: Apr. 22, 2021

(65) Prior Publication Data

US 2021/0346341 A1 Nov. 11, 2021

Related U.S. Application Data

(60) Provisional application No. 63/020,261, filed on May 5, 2020.

(51) Int. Cl.
*A61P 25/22* (2006.01)
*A61K 31/36* (2006.01)
*A61K 31/48* (2006.01)
*A61P 25/24* (2006.01)

(52) U.S. Cl.
CPC .............. *A61K 31/36* (2013.01); *A61K 31/48* (2013.01); *A61P 25/22* (2018.01)

(58) Field of Classification Search
CPC .................. A61P 25/22; A61P 25/24
See application file for complete search history.

(56) References Cited

U.S. PATENT DOCUMENTS

| 11,364,221 B2 * | 6/2022 | Liechti .................. A61P 25/22 |
| 2018/0221396 A1 | 8/2018 | Chadeayne |
| 2020/0147038 A1 | 5/2020 | Russ et al. |

FOREIGN PATENT DOCUMENTS

| WO | 2016199135 | † 12/2016 |
| WO | 2020157569 | † 8/2020 |
| WO | 2021202730 | † 10/2021 |

OTHER PUBLICATIONS

Ahearn, J. Psychiat Res. 1997, vol. 31(5), pp. 569-579. (Year: 1997).*

(Continued)

*Primary Examiner* — Craig D Ricci
*Assistant Examiner* — Janet L Coppins
(74) *Attorney, Agent, or Firm* — Kohn and Associates PLLC

(57) ABSTRACT

A method of enhancing positive effects of a psychedelic, by inducing a positive psychological state in an individual with an empathogen/entactogen, administering a psychedelic to the individual, and enhancing a positive response to the psychedelic. A composition including an entactogen/empathogen and a serotonergic psychedelic in the same dosage form or administered as separate compositions within a combination treatment schedule. A method of enhancing positive effects of a psychedelic, by inducing the release of endogenous monoamines, and subsequently stimulating 5-HT$_{2A}$ receptors.

4 Claims, 15 Drawing Sheets

(56) References Cited

OTHER PUBLICATIONS

Sessa and Fischer, Drug Science, Policy and Law 2015, vol. 2, pp. 1-8. (Year: 2015).*
Liechti et al, Psychopharmacology(2017)234:1499-1510 (Year: 2017).*
Knapp et al, Journal of Immunology 322, 2018, pp. 74-80. (Year: 2018).*
Schechter, M.D., European Journal of Pharmacology 1998, 341(2-3), pp. 131-134 (Year: 1998).*
Ly et al., Cell Reports 23 (2018), pp. 3170-3182. (Year: 2018).*
Barrett FS, Preller KH, Herdener M, Janata P, Vollenweider FX (2018). Serotonin 2A Receptor Signaling Underlies LSD-induced Alteration of the Neural Response to Dynamic Changes in Music. Cereb Cortex 28: 3939-3950.
Bershad AK, Miller MA, Baggott MJ, de Wit H (2016a). The effects of MDMA on socio-emotional processing: does MDMA differ from other stimulants? J Psychopharmacol 30: 1248-1258.
Bershad AK, Weafer JJ, Kirkpatrick MG, Wardle MC, Miller MA, de Wit H (2016b). Oxytocin receptor gene variation predicts subjective responses to MDMA. Soc Neurosci 11: 592-599.
Carhart-Harris RL, Kaelen M, Bolstridge M, Williams TM, Williams LT, Underwood R, et al. (2016). The paradoxical psychological effects of lysergic acid diethylamide (LSD). Psychol Med 46: 1379-1390.
Dittrich A (1998). The standardized psychometric assessment of altered states of consciousness (ASCs) in humans. Pharmacopsychiatry 31 (Suppl 2): 80-84.
Dolder PC, Schmid Y, Mueller F, Borgwardt S, Liechti ME (2016). LSD acutely impairs fear recognition and enhances emotional empathy and sociality. Neuropsychopharmacology 41: 2638-2646.
Dolder PC, Muller F, Schmid Y, Borgwardt SJ, Liechti ME (2018). Direct comparison of the acute subjective, emotional, autonomic, and endocrine effects of MDMA, methylphenidate, and modafinil in healthy subjects. Psychopharmacology 235: 467-479.
Dolder PC, Schmid Y, Steuer AE, Kraemer T, Rentsch KM, Hammann F, et al. (2017). Pharmacokinetics and pharmacodynamics of lysergic acid diethylamide in healthy subjects. Clin Pharmacokinetics 56: 1219-1230.
Farre M, Abanades S, Roset PN, Peiro AM, Torrens M, O'Mathuna B, et al. (2007). Pharmacological interaction between 3,4-methylenedioxymethamphetamine (ecstasy) and paroxetine: pharmacological effects and pharmacokinetics. J Pharmacol Exp Ther 323: 954-962.
Gallimore AR, Strassman RJ (2016). A model for the application of target-controlled intravenous infusion for prolonged immersive DMT psychedelic experience. Front Pharmacol doi: 10.3389/fphar.2016.00211.
Garcia-Romeu A, Griffiths RR, Johnson MW (2015). Psilocybin-occasioned mystical experiences in the treatment of tobacco addiction. Curr Drug Abuse Rev 7: 157-164.
Griffiths R, Richards W, Johnson M, McCann U, Jesse R (2008). Mystical-type experiences occasioned by psilocybin mediate the attribution of personal meaning and spiritual significance 14 months later. J Psychopharmacol 22: 621-632.
Griffiths RR, Johnson MW, Carducci MA, Umbricht A, Richards WA, Richards BD, et al. (2016). Psilocybin produces substantial and sustained decreases in depression and anxiety in patients with life-threatening cancer: a randomized double-blind trial. J Psychopharmacol 30: 1181-1197.
Hasler F, Grimberg U, Benz MA, Huber T, Vollenweider FX (2004). Acute psychological and physiological effects of psilocybin in healthy humans: a double-blind, placebo-controlled dose-effect study. Psychopharmacology 172: 145-156.
Hintzen A, Passie T (2010). The pharmacology of LSD: a critical review. edn. Oxford University Press: Oxford.
Holze F, Duthaler U, Vizeli P, Muller F, Borgwardt S, Liechti ME (2019a). Pharmacokinetics and subjective effects of a novel oral LSD formulation in healthy subjects. Br J Clin Pharmacol 85: 1474-1483.
Holze F, Vizeli P, Muller F, Ley L, Duerig R, Varghese N, et al. (2019b). Distinct acute effects of LSD, MDMA, and D-amphetamine in healthy subjects. Neuropsychopharmacology.
Hysek CM, Simmler LD, Ineichen M, Grouzmann E, Hoener MC, Brenneisen R, et al. (2011). The norepinephrine transporter inhibitor reboxetine reduces stimulant effects of MDMA ("ecstasy") in humans. Clinical pharmacology and therapeutics 90: 246-255.
Hysek CM, Simmler LD, Schillinger N, Meyer N, Schmid Y, Donzelli M, et al. (2014a). Pharmacokinetic and pharmacodynamic effects of methylphenidate and MDMA administered alone and in combination. Int J Neuropsychopharmacol 17: 371-381.
Hysek CM, Simmler LD, Nicola V, Vischer N, Donzelli M, Krähenbühl S, et al. (2012). Duloxetine inhibits effects of MDMA ("ecstasy") in vitro and in humans in a randomized placebo-controlled laboratory study. PLoS One 7: e36476.
Hysek CM, Schmid Y, Simmler LD, Domes G, Heinrichs M, Eisenegger C, et al. (2014b). MDMA enhances emotional empathy and prosocial behavior. Soc Cogn Affect Neurosci 9: 1645-1652.
Kammermann J, Stieglitz RD, & Riecher-Rossler A (2009). Self-screen prodrome—self-rating for the early detection of mental disorders and psychoses. Fortschr Neurol Psychiatr 77: 278-284.
Kirkpatrick MG, Francis SM, Lee R, de Wit H, Jacob S (2014). Plasma oxytocin concentrations following MDMA or intranasal oxytocin in humans. Psychoneuroendocrinology 46: 23-31.
Kraehenmann R, Pokorny D, Vollenweider L, Preller KH, Pokorny T, Seifritz E, et al. (2017). Dreamlike effects of LSD on waking imagery in humans depend on serotonin 2A receptor activation. Psychopharmacology 234: 2031-2046.
Liechti ME (2017). Modern clinical research on LSD. Neuropsychopharmacology 42: 2114-2127.
Liechti ME, Vollenweider FX (2000a). The serotonin uptake inhibitor citalopram reduces acute cardiovascular and vegetative effects of 3,4-methylenedioxymethamphetamine ('Ecstasy') in healthy volunteers. J Psychopharmacol 14: 269-274.
Liechti ME, Vollenweider FX (2001). Which neuroreceptors mediate the subjective effects of MDMA in humans? A summary of mechanistic studies. Human psychopharmacology 16: 589-598.
Liechti ME, Baumann C, Gamma A, Vollenweider FX (2000b). Acute psychological effects of 3,4-methylenedioxymethamphetamine (MDMA, "Ecstasy") are attenuated by the serotonin uptake inhibitor citalopram. Neuropsychopharmacology 22: 513-521.
Liechti ME, Saur MR, Gamma A, Hell D, Vollenweider FX (2000c). Psychological and physiological effects of MDMA ("Ecstasy") after pretreatment with the 5-HT(2) antagonist ketanserin in healthy humans. Neuropsychopharmacology 23: 396-404.
Marona-Lewicka D, Nichols DE (2007). Further evidence that the delayed temporal dopaminergic effects of LSD are mediated by a mechanism different than the first temporal phase of action. Pharmacology, biochemistry, and behavior 87: 453-461.
Marona-Lewicka D, Thisted RA, Nichols DE (2005). Distinct temporal phases in the behavioral pharmacology of LSD: dopamine D2 receptor-mediated effects in the rat and implications for psychosis. Psychopharmacology 180: 427-435.
Mittman SM, Geyer MA (1991). Dissociation of multiple effects of acute LSD on exploratory behavior in rats by ritanserin and propranolol. Psychopharmacology 105: 69-76.
Nichols DE (2016). Psychedelics. Pharmacological reviews 68: 264-355.
Nichols DE, Grob CS (2018). Is LSD toxic? Forensic science international 284: 141-145.
Passie T, Halpern JH, Stichtenoth DO, Emrich HM, Hintzen A (2008). The pharmacology of lysergic acid diethylamide: a review. CNS Neurosci Ther 14: 295-314.
Preller KH, Herdener M, Pokorny T, Planzer A, Kraehenmann R, Stampfli P, et al. (2017). The fabric of meaning and subjective effects in LSD-induced states depend on serotonin 2A receptor activation Curr Biol 27: 451-457.
Ramos L, Hicks C, Caminer A, Couto K, Narlawar R, Kassiou M, et al. (2016). MDMA ('Ecstasy'), oxytocin and vasopressin modulate social preference in rats: A role for handling and oxytocin receptors. Pharmacology, biochemistry, and behavior 150-151: 115-123.

(56) References Cited

OTHER PUBLICATIONS

Rickli A, Moning OD, Hoener MC, Liechti ME (2016). Receptor interaction profiles of novel psychoactive tryptamines compared with classic hallucinogens. European neuropsychopharmacology : the journal of the European College of Neuropsychopharmacology 26: 1327-1337.
Roseman L, Nutt DJ, Carhart-Harris RL (2017). Quality of acute psychedelic experience predicts therapeutic efficacy of psilocybin for treatment-resistant depression. Front Pharmacol 8: 974.
Ross S, Bossis A, Guss J, Agin-Liebes G, Malone T, Cohen B, et al. (2016). Rapid and sustained symptom reduction following psilocybin treatment for anxiety and depression in patients with life-threatening cancer: a randomized controlled trial. J Psychopharmacol 30: 1165-1180.
Schmid Y, Liechti ME (2018). Long-lasting subjective effects of LSD in normal subjects. Psychopharmacology 235: 535-545.
Schmid Y, Hysek CM, Simmler LD, Crockett MJ, Quednow BB, Liechti ME (2014). Differential effects of MDMA and methylphenidate on social cognition. J Psychopharmacol 28: 847-856.
Schmid Y, Enzler F, Gasser P, Grouzmann E, Preller KH, Vollenweider FX, et al. (2015). Acute effects of lysergic acid diethylamide in healthy subjects. Biol Psychiatry 78: 544-553.
Simmler L, Buser T, Donzelli M, Schramm Y, Dieu LH, Huwyler J, et al. (2013). Pharmacological characterization of designer cathinones in vitro. Br J Pharmacol 168: 458-470.
Strassman RJ (1996). Human psychopharmacology of N,N-dimethyltryptamine. Behav Brain Res 73: 121-124.
Strassman RJ, Qualls CR (1994a). Dose-response study of N,N-dimethyltryptamine in humans: I. Neuroendocrine, autonomic, and cardiovascular effects. Archives of general psychiatry 51: 85-97.
Strassman RJ, Qualls CR, Uhlenhuth EH, Kellner R (1994b). Dose-response study of N,N-dimethyltryptamine in humans: II. Subjective effects and preliminary results of a new rating scale. Archives of general psychiatry 51: 98-108.
Studerus E, Gamma A, Kometer M, Vollenweider FX (2012). Prediction of psilocybin response in healthy volunteers. PLoS One 7: e30800.
Tancer M, Johanson CE (2003). Reinforcing, subjective, and physiological effects of MDMA in humans: a comparison with d-amphetamine and mCPP. Drug and alcohol dependence 72: 33-44.
Timmermann C, Roseman L, Schartner M, Milliere R, Williams LTJ, Erritzoe D, et al. (2019). Neural correlates of the DMT experience assessed with multivariate EEG. Sci Rep 9: 16324.
Verrico CD, Miller GM, Madras BK (2007). MDMA (ecstasy) and human dopamine, norepinephrine, and serotonin transporters: implications for MDMA-induced neurotoxicity and treatment. Psychopharmacology 189: 489-503.
Vizeli P, Liechti ME (2017). Safety pharmacology of acute MDMA administration in healthy subjects. J Psychopharmacol 31: 576-588.
Vizeli P, Liechti ME (2018). Oxytocin receptor gene variations and socio-emotional effects of MDMA: A pooled analysis of controlled studies in healthy subjects. PLoS One 13: e0199384.
Wittchen HU, Wunderlich U, Gruschwitz S, & Zaudig M (1997) SKID-I: Strukturiertes Klinisches Interview für DSM-IV. Hogrefe-Verlag: Göttingen.
Zerssen DV (1976) Die Beschwerden-Liste. Münchener Informationssystem. Psychis: München.
Liechti, Alterations of consciousness and mystical-type experiences after acute LSD in humans, vol. 234 p. 1499-1510, 2017, Psychopharmacology.†

Sessa, Underground MDMA-, LSD- and 2-CB-assisted individual and group psychotherapy in Zurich: Outcomes, implications and commentary, vol. 2(0) pp. 1-8, 2015, Drug Science, Policy and Law.†
Liechti, Gender differences in the subjective effects of MDMA, vol. 154 pp. 161-168, 2001, Psychopharmacology.†
Licht, Simultaneous polysubstance use among Danish 3,4-methylenedioxymethamphetamine and hallucinogen users: combination patterns and proposed biological bases, vol. 27 pp. 352-363, 2012, Human Psychopharmacology: Clinical and Experimental.†
Schechter, Candyflipping: Synergistic discriminative effect of LSD and MDMA, vol. 341(2-3) pp. 131-134, 1998, European Journal of Pharmacology.†
White, The Effects of Methylenedioxymethamphetamine (MDMA, 'Ecstasy') on Monoaminergic Neurotransmission in the Central Nervous System, vol. 49 pp. 455-479, 1996, Progress in Neurobiolog.†
Boys, Understanding reasons for drug use amongst young people a functional perspective, vol. 16(4) pp. 457-469, 2001, Health Education Research.†
Olson, Tripping on nothing: placebo psychedelics and contextual factors, vol. 237 pp. 1371-1382, 2020, Psychopharmacology.†
Holze, Distinct acute effects of LSD, MDMA, and d-amphetamine in healthy subjects, vol. 45 pp. 462-471, 2019, Neuropsychopharmacology.†
Santos-Longhurst, LSD and MDMA: What to Know About Candyflipping, 2020, retrieved from Healthline.com, Feb. 2, 2020, retrieved from Web Archive Feb. 11, 2020, https://web.archive.org/web/20200211232126/https://www.healthline.com/health/lsd-and-mdma.†
Smigielski, Characterization and prediction of acute and sustained response to psychedelic psilocybin in a mindfulness group retreat, vol. 9 pp. 1-13, 2019, Scientific Reports.†
Chary, Candyflipping and Other Combinations: Identifying Drug-Drug Combinations from an Online Forum, vol. 9 pp. 1-9, 2018, Frontiers Psychiatry.†
Halberstadt, Behavioral Neurobiology of Psychedelic Drugs, 2018, Springer, ISBN: 978-3-662-55878-2.†
Van Well, Effects of Acute MDMA Intoxication on Mood and Impulsivity: Role of the 5-HT2 and 5-HT1 Receptors, vol. 7(7) pp. 1-8, 2012, PLoS One.†
DMT-NEXUS, Known substance-interactions and their effects, 2013, retrieved from wiki.dmt-nexus.me, Dec. 14, 2012, retrieved from Web Archive Jan. 25, 2013, https://web.archive.org/web/20130125065447/https://wiki.dmt-nexus.me/Known_substance-interactions_and_their_effects.†
Danforth, MDMA-assisted therapy: A new treatment model for social anxiety in autistic adults, vol. 64 pp. 237-249, 2016, Progress in Neuro-Psychopharmacology and Biological Psychiatry.†
B-E-H, Inc., Searching for Samadhi in West Philadelphia LSD, MDMA (Ecstacy) & Alcohol, 2012, 7 retrieved from Erowid.org, Jan. 7, 2012, retrieved from Web Archive Jan. 20, 2012, https://web.archive.org/web/20120120044616/https://erowid.org/experiences/exp.php?ID=79281.†
Kryptonite, A Glorious New Year LSD & MDMA (Ecstasy), 2009, retrieved from Erowid.org, Jul. 19, 2009, retrieved from Web Archive Jul. 4, 2010, https://web.archive.org/web/20100704210848/https://www.erowid.org/experiences/exp.php?ID=58609.†

\* cited by examiner
† cited by third party

LSD

MDMA

MDMA TREATMENT TO ENHANCE ACUTE EMOTIONAL EFFECTS PROFILE OF LSD, PSILOCYBIN, OR OTHER PSYCHEDELICS

BACKGROUND OF THE INVENTION

1. Technical Field

The present invention relates to compositions and methods of enhancing emotional and therapeutic effects of psychedelics.

2. Background Art

LSD (lysergic acid diethylamide, FIG. 1A) can be used to assist psychotherapy for many indications including anxiety, depression, addiction, personality disorder and others and can also be used to treat other disorders such as cluster headache and migraine and others (Passie et al., 2008; Hintzen et al., 2010; Nichols, 2016; Liechti, 2017).

The acute subjective effects of LSD are mostly positive in most humans (Schmid et al., 2015; Carhart-Harris et al., 2016; Dolder et al., 2016; Dolder et al., 2017; Holze et al., 2019a). However, there are also negative subjective effects (anxiety) of LSD in many humans depending on the dose of LSD used, personality traits (set) of the person using LSD, the setting (environment), and other factors. The risk of acute negative psychological effects is the main problem of use of psychedelic substances in humans. Anxiety when occurring in LSD-assisted psychotherapy may become a significant problem for both the patient and treating physician. In addition to being highly distressing to the patient, acute anxiety has been linked to a non-favorable long-term outcome in patients with depression (Roseman et al., 2017). Furthermore, anxiety reactions during psychedelic-assisted therapy may require additional supervision, greater engagement of therapists, prolonged sessions, and acute psychological and also pharmacological interventions. Thus, the primary safety concerns relate to psychological rather than somatic adverse effects (Nichols, 2016; Nichols et al., 2018). The induction of an overall positive acute response to the psychedelic is critical because several studies showed that a more positive experience is predictive of a greater therapeutic long-term effect of the psychedelic (Garcia-Romeu et al., 2015; Griffiths et al., 2016; Ross et al., 2016). Even in healthy subjects, positive acute responses to psychedelics including LSD has been shown to be linked to more positive long-term effects on well-being (Griffiths et al., 2008; Schmid et al., 2018).

Moderate anticipatory anxiety is common at the beginning of the onset of a drug's effects (Studerus et al., 2012). In a study in sixteen healthy humans, after administration of 0.2 mg of LSD marked anxiety was observed in two subjects. This anxiety was related to fear of loss of thought control, disembodiment, and loss of self (Schmid et al., 2015) and similarly described for psilocybin (Hasler et al., 2004). Bad drug effects (50% or more on a 0-100% scale at any time point after drug administration) were noted in 9 of 16 subjects (56%) after a high dose of 0.2 mg of LSD and in 3 of 24 subjects (12.5%) after a moderate 0.1 mg dose of LSD (Dolder et al., 2017). Similarly, another study reported transient bad drug effects in 7 of 24 subjects (29%) after administration of 0.1 mg of LSD (Holze et al., 2019a). Although, these negative subjective drug effects were transient and occurred in subjects who all also reported good drug effects at other or similar time points, negative responses are an issue. One solution to address negative drug effects is to reduce the dose of the psychedelic but this would also reduce at least in part the good drug effects. Dose optimization is being performed and 0.1 mg of LSD may be a dose with a more favorable acute effect profile in most subjects compared with 0.2 mg of LSD.

An important factor contributing to negative responses to LSD is the state of mood before and during the onset of the LSD response. Previously published studies showed that positive mood before administration of the psychedelic psilocybin is positively correlated with a more positive and therefore likely more beneficial therapeutic response to psilocybin. Specifically, greater activity and emotional excitability in an adjective mood rating scale (AMRS) predicted greater oceanic boundlessness after psilocybin use (Studerus et al., 2012). Greater oceanic boundlessness in response to psilocybin has been linked with greater antidepressant long-term effects of psilocybin (Roseman et al., 2017). Based on this information enhancing positive mood prior and during administration of a psychedelic can be expected to improve the positive versus negative effects profile.

There remains a need for methods of reducing bad drug effects that can prejudice the patient treatment outcome while enhancing good drug effects which can optimize the patient treatment outcome with psychedelic administration.

SUMMARY OF THE INVENTION

The present invention provides for a method of enhancing positive effects of a psychedelic, by inducing a positive psychological state in an individual with an empathogen/entactogen, administering a psychedelic to the individual, and enhancing a positive response to the psychedelic.

The present invention provides for a composition including an entactogen/empathogen and a serotonergic psychedelic in the same dosage form or administered as separate compositions within a combination treatment schedule.

The present invention also provides for a method of enhancing positive effects of a psychedelic, by inducing the release of endogenous monoamines, and subsequently stimulating 5-HT2A receptors.

The present invention also provides for a method of treating a patient by enhancing the mood of the patient prior to psychedelic treatment.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

The present invention provides for methods of enhancing (qualitatively positively improving) the acute subjective (emotional, therapeutic) action of psychedelics in treatment for medical (mainly psychiatric) conditions. More specifically, the present invention provides for a method of enhancing positive acute and long-term therapeutic effects of a psychedelic, by inducing a positive psychological state in an individual, administering a psychedelic to the individual, and enhancing the positive response to the psychedelic. The overall goal of the present invention is to improve the positive over negative acute subjective effect response (i.e. improve good drug effects over and reduce bad drug effects) to a psychedelic. The method can be used for any indication of psychedelic medication use and typically applies to indications where a positive experience after psychedelic use predicts the long-term effects such as in psychiatric disorders including (but no limited to) depression, anxiety, anxiety related to life-threatening disease, obsessive-compulsive disorder, personality disorder, and addiction.

"Bad drug effects" as used herein refers to any unwanted effects of the psychedelic, such as, but not limited to anxiety, fear, fear of loss of body control, anxious-ego dissolution, disembodiment, fear of impaired thought control, paranoia, panic, negative thoughts, grooming, "nadir" effects, or generally negative acute drug effects as self-rated by healthy subjects or patients in studies using psychedelics, and combinations thereof.

"Good drug effects" as used herein refers to any desired effects of the psychedelic, such as, but not limited to good drug effects, drug linking, oceanic boundlessness, experience of unity, spiritual experience, blissful state, insightfulness, connectedness, mystical experiences, mystical-type effects, positive mood, transcendence of time/space, ineffability, well-being, trust, feelings of love, feeling open, peak experience, and combinations thereof.

"Treatment outcome" as used herein refers to any change (improvement) in a disorder for which psychedelic-therapy is used and lasting longer than the acute effects of the substances. For example, a good drug effect acutely induced with a psychedelic is known to improve depression in patients with depression and treated with a psychedelic beyond the acute effect of the psychedelic.

Figure 1A:
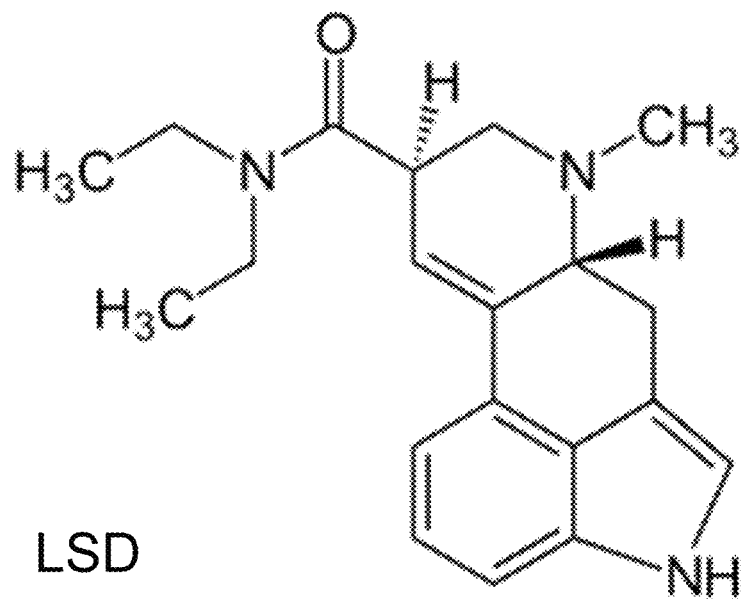
FIG. 1A is the chemical structure of LSD and FIG. 1B is the chemical structure of MDMA.
Figure 1B:
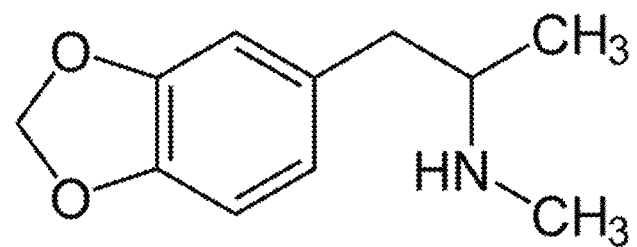

Most preferably, the step of inducing a positive psychological state is accomplished by administering to the individual an empathogen/entactogen or 3,4-methylenedioxymethamphetamine (MDMA)-like compound such as but not limited to MDMA (FIG. 1B), 3,4-methylendioxyamphetamine (MDA), 3,4,-methylenedioxyethylamphetamine (MDEA), 5,6-methylenedioxy-2-aminoindane (MDAI), mephedrone, methylone, 3-MMC, homologues thereof, analogues thereof, or novel compounds or prodrugs resulting in a similar MDMA-type acute subjective effect profile. Any other compound that provides a similar MDMA-type acute subjective effect profile can also be used. MDMA has previously been shown to induce a state of well-being including increased activation and emotional excitation (Hysek et al., 2011; Hysek et al., 2014b) and this emotional state is known to be associated with a better response to psychedelics (Studerus et al., 2012). MDMA also induces feelings of trust, increased empathy and relaxation (Hysek et al., 2014b; Schmid et al., 2014) expected to facilitate the LSD experience and to reduce anticipation anxiety. MDMA is preferably administered in a dose of 20-200 mg. Mechanisms of action of MDMA are described below.

The psychedelics used in the methods of the present invention can be, but are not limited to, psilocybin, psilocin, lysergic acid diethylamide (LSD), mescaline, dimethyltryptamine (DMT), 2,5-dimethoxy-4-iodoamphetamine (DOI), 2,5-dimethoxy-4-bromoamphetamie (DOB), other phenethylamine or tryptamine psychedelics, salts thereof, analogs thereof, or prodrugs thereof, or homologues thereof. Any suitable dose can be used, and several examples are provided below. Mechanisms of action of the psychedelics are described below.

Doses commonly used in LSD-assisted treatment/psychotherapy are 0.1-0.2 mg. A dose of 0.1 mg produced subjective effects in humans lasting (mean±SD) 8.5±2.0 hours (range: 5.3-12.8 hours) in one representative study (Holze et al., 2019a). Times of onset and offset of the subjective response, assessed by the "any drug effect" Visual Analog Scales (VAS), were (mean±SD) 0.7±0.2 hours (range 0.3-1.0 hours) and 9.1±2.0 hours (range: 6.0-13.2 hours), respectively (Holze et al., 2019a). The time to the subjective peak effect of LSD is 2.5±0.6 hours (range 1.6-4.3 hours) (Holze et al., 2019a). In other studies, LSD effects similarly lasted 8.2±2.1 hours (range: 5-14 hours) after administration of a 0.1 mg dose and 11.6±1.7 hours (range: 7-19.5 hours) after administration of a 0.2 mg dose (Dolder et al., 2017). The time to the subjective peak effect of LSD is 2.5±0.6 hours (range 1.6-4.3 hours) (Holze et al., 2019a). Anxiety mostly occurs during the peak effects of LSD 1-4 hours after the administration of an oral dosing formulation (Dolder et al., 2017; Holze et al., 2019a).

MDMA produces its positive mood effects over a shorter time than LSD (Holze et al., 2019b). The onset of the MDMA effect after oral administration occurs at (mean±SD) 33±24 minutes and the peak effect is reached 1.6±0.8 hours after MDMA administration. The duration of the subjective effect is 4.2±1.3 hours (Vizeli et al., 2017).

In the present invention, MDMA can be administered before, at the same time, or less typically after administering the psychedelic or even before and after depending on pharmacokinetics of the formulation to be used. In one example using LSD, assuming administration at the same time as LSD and using oral administration of both substances, the MDMA effect starts on average after 33 minutes and the effect of LSD on average after 42 minutes. MDMA and LSD peak effects are then reached at 1.6 hours and 2.5 hours, respectively. Thus, as mainly intended by the present invention the MDMA effect will establish before and during the start of the potentially overwhelming psychedelic response with the intention of avoiding or reducing anxiety. The MDMA effect is expected to be additive or sub-additive to the psychedelic response. Importantly, the subjective response to LSD is clearly more pronounced even at moderate doses of LSD (0.1 mg) compared to that of even a high dose of MDMA (125 mg) (Holze et al., 2019b). It is therefore not expected that the subjective effect of both substances is substantially greater than that of LSD alone but different in quality (overall more positive). Slightly higher autonomic effects are expected compared to the administration of either substance alone, but the overall response is predicted to be sub-additive or additive at most based on the data on the combined use of more strongly stimulating substances in combination with MDMA (Hysek et al., 2014a).

Typical doses likely to be used in the context of the present invention are MDMA: 20-200 mg and LSD 0.05-0.3 mg, with a dose of MDMA of 100 mg and of LSD of 0.1 mg being average and typical doses to be used as shown in EXAMPLE 1. It is expected that the MDMA effect will not last as long as the response to the psychedelic. Accordingly, it is expected that MDMA will produce a more positive response to psychedelic and reduced anxiety up to 6 hours after drug administration. Thereafter, the effects of the psychedelic are substantially lower compared to its peak response and will decline over another 3-6 hours. It is possible that a more positive response to the psychedelic during the first 6 hours will also result in reduced anxiety during the hours thereafter.

Additionally, the use of MDMA with other shorter-acting psychedelics such as psilocybin can result in more aligned duration of action of the two substances. Specifically, the duration of action of psilocybin is 4-6 hours (Passie et al., 2008; Griffiths et al., 2016) and similar to that of MDMA. When combined with psilocybin, MDMA can be administered also before, at the same time, or after psilocybin but for the purpose of the invention administration will occur best before or with psilocybin. When combined with very short-acting psychedelics such as intravenous DMT or inhaled DMT (Strassman et al., 1994a; Strassman et al., 1994b; Strassman, 1996; Gallimore et al., 2016; Timmermann et al., 2019), administration of MDMA can take place 1-2 hours before DMT to fully establish the desired positive mood effects when the DMT effects start. The response to MDMA can then last longer than that of the short acting psychedelic (DMT).

Mechanistically, psychedelics act as serotonin 5-HT2A receptor agonists. LSD potently stimulates the 5-HT2A receptor but also 5-HT2B/C, 5-HT1 and D1-3 receptors (Rickli et al., 2016). LSD induces its psychedelic effects in humans primarily via stimulation of the 5-HT2A receptor (Kraehenmann et al., 2017; Preller et al., 2017; Barrett et al., 2018). Psilocin, the active metabolite of psilocybin, inhibits the 5-HT transporter (SERT) whereas LSD stimulates D1-3 receptors but does not interact with the SERT (Rickli et al., 2016). In contrast to LSD, psilocybin and mescaline show no affinity for D2 receptors. The potent dopaminergic receptor agonist properties of LSD have been linked to delayed LSD effects that are possibly distinct from other hallucinogens and possibly more stimulant-like (Mittman et al., 1991; Marona-Lewicka et al., 2005; Marona-Lewicka et al., 2007; Nichols, 2016). LSD and the tryptamines DMT and psilocin are potent agonists at serotonin 5-HT1 receptors while other hallucinogens such as mescaline exhibit low potency at this receptor (Rickli et al., 2016). While no clinical studies have clearly documented a role for the 5-HT1 receptor (Strassman, 1996; Nichols, 2016) in the action of psychedelics, differences between substances may exist. SERT inhibition (Rickli et al., 2016) and increases in serotonin by psilocybin may be associated with greater serotonergic toxicity including nausea and vomiting when psilocybin is used compared to other psychedelics with no interaction with the SERT. Mescaline binds in a similar concentration range to 5-HT2A, 5-HT1A and adrenergic α2A receptors (Rickli et al., 2016). Whether all these molecular differences have an influence on the subjective effects and on alterations of consciousness has not yet been studied in humans and this will need to be further explored to better substantiate any claims related to benefits of LSD over psilocybin (ongoing study). MDMA mainly acts as a releaser of serotonin and norepinephrine and to a lesser extent dopamine (Verrico et al., 2007; Simmler et al., 2013). Compared with amphetamine, the typical mood effects of MDMA can be predominantly attributed to activation of the 5-HT system (Liechti et al., 2000b; Liechti et al., 2000c; Liechti et al., 2000a; Liechti et al., 2001; Tancer et al., 2003; Farre et al., 2007; Hysek et al., 2012; Hysek et al., 2014b; Schmid et al., 2014; Bershad et al., 2016a; Dolder et al., 2018). It is possible that release of oxytocin also contributes to the positive mood effects of MDMA (Hysek et al., 2014b; Kirkpatrick et al., 2014; Bershad et al., 2016b; Ramos et al., 2016; Vizeli et al., 2018). Thus, compared with the administration of a psychedelic alone, the addition of MDMA results in release of monoamines and oxytocin. It is this additional pharmacological effect of MDMA that produces a distinct and postulated more positive overall mood response to psychedelics. In the case of co-treatment with LSD, MDMA can act at the time of the peak response and less during the late response to LSD where its dopaminergic late effects may predominate (Mittman et al., 1991; Marona-Lewicka et al., 2005; Marona-Lewicka et al., 2007; Nichols, 2016). Thus, in the MDMA-LSD combination, dopaminergic activity can result at the beginning through the action of MDMA and more by the direct action of LSD later in time. In the case of the MDMA-psilocybin combination no late phase is present and the effects are expected to be mainly shorter compared with the MDMA-LSD combination but otherwise relatively similar in quality of the experience. Psilocybin acts for approximately 4-6 hours (Passie et al., 2008; Griffiths et al., 2016). Thus, its duration of action is similar to that of MDMA (Vizeli et al., 2017). In contrast to psychedelics, MDMA-type substances induce the release of endogenous monoamines (serotonin, norepinephrine, and dopamine) with a preference of release of serotonin over dopamine. While both mechanisms have been well described and characterized, the present invention shows that adding release of serotonin and dopamine (by adding an MDMA-type substance effect) to direct 5-HT2A receptor stimulation (by a psychedelic) will enhance the positive over negative mood effect profile of a psychedelic and improve its therapeutic potential.

Therefore, the present invention also provides for a method of enhancing positive effects of a psychedelic, by inducing the release of endogenous monoamines, and subsequently stimulating 5-HT2A receptors.

The present invention also provides for a method of treating a patient by enhancing the mood of the patient prior to psychedelic treatment. Administering the empathogen/entactogen enhances the patient's mood by providing a positive mood. A positive mood can be provided by increasing positive acute effects and decreasing negative acute effects.

"Positive acute effects" as used herein refers primarily to an increase in subjective rating of good drug effect, and can also include ratings of drug liking, well-being, trust, feelings of love, openness, oceanic boundlessness, experience of unity, spiritual experience, blissful state, insightfulness, any mystical-type experience, and positively experienced psychedelic effects, and aspects of ego-dissolution if experienced without anxiety.

"Negative acute effects" as used herein refers primarily to subjective ratings of bad drug effect, anxiety, and fear and can additionally include increased ratings of anxious ego-dissolution, or descriptions of acute paranoia or states of panic and anxiety as observed by others.

The MDMA and psychedelics can be in separate dosage forms administered to the individual at separate times in a dosing schedule or in the same dosage form with different release profiles in order to achieve the desired effects of producing the MDMA effect before or with the acute effects of the psychedelic. Therefore, the present invention provides for a composition including MDMA and a psychedelic in the same dosage form. It should be understood that the compounds can also be in separate dosage forms administered within the same treatment session.

The method of the present invention provides overall more positive effects with psychedelics when co-administered with MDMA compared with psychedelics alone at the same dose, as shown by EXAMPLE 1. The method also allows for the use of psychedelics at higher dose that would normally be associated with more adverse effects (anxiety) but would also produce greater long-term effects than a low dose by co-using MDMA to make the acute experience more positive. Individuals suitable for such combined use are: 1) persons with negative experience in the past, 2) persons with trait characteristics know to be associated with more negative responses, and 3) persons needing a higher dose of psychedelics due to non-response in previous treatments.

The compounds of the present invention are administered and dosed in accordance with good medical practice, considering the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that it can be administered as the compound and can be administered alone or as an active ingredient in combination with pharmaceutically acceptable carriers, diluents, adjuvants, and vehicles. The compounds can be administered orally, subcutaneously, or parenterally including intravenous, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple single doses separated by several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

EXAMPLE 1: CLINICAL STUDY: EFFECTS OF MDMA CO-ADMINISTRATION ON THE RESPONSE TO LSD IN HEALTHY SUBJECTS (LSD-MDMA STUDY)

The study determined the qualitative emotional differences between a combined LSD/MDMA experience and a pure LSD experience, also including a pure MDMA and placebo control condition. It was hypothesized that subjects under the LSD-MDMA condition would experience increased pleasurable subjective effects (increased "good drug effect", "trust", and "openness" and less "bad drug effects" and "anxiety" in the VAS [good/bad drug effect ratio in the VAS]), increased general well-being (in the AMRS), and increased OB and reduced anxiety/AED (OB/AED scale ratio in the 5D-ASC) compared to LSD administered alone. It was expected that the combined administration of LSD and MDMA would not elevate cardiovascular parameters significantly compared to MDMA administered alone.

Materials and Methods

Study design: This study used a single-center randomized, double-blind, cross-over design with 4 conditions: (1) 0.1 mg LSD, (2) 100 mg MDMA, (3) 0.1 mg LSD+100 mg MDMA, (4) Placebo. Study days encompassed a 14-hour study day with a subsequent single measurement the next morning (24 hours after drug administration). Each subject participated in 4×14-hour study sessions separated by at least 10 days. Study substances were administered in pre-prepared vials (LSD) and capsules (MDMA) which were assigned to each participant in a randomized manner prior to study commencement. Placebo vials (containing only alcohol) and placebo capsules (containing only mannitol) looked identical to those containing the active substances to ensure proper blinding.

Participants: The preliminary study included healthy subjects (male and females). Inclusion criteria were: age between 25 and 65 years old; sufficient understanding of the German language; understanding of procedures and risks associated with the study; willing to adhere to the protocol and signing of the consent form; willing to refrain from the consumption of illicit psychoactive substances during the study; abstaining from xanthine-based liquids from the evenings prior to the study sessions to the end of the study days; willing not to operate heavy machinery within 48 hours after substance administration; willing to use double-barrier birth control throughout study participation; and body mass index between 18-29 kg/m2. Exclusion criteria were: chronic or acute medical condition; current or previous major psychiatric disorder; psychotic disorder or bipolar disorder in first-degree relatives; hypertension (>140/90 mmHg) or hypotension (SBP<85 mmHg); hallucinogenic substance use (not including *cannabis*) more than 20 times or any time within the previous two months; pregnancy or current breastfeeding; participation in another clinical trial (currently or within the last 30 days); use of medication that may interfere with the effects of the study medication; tobacco smoking (>10 cigarettes/day); and consumption of alcoholic beverages (>20 drinks/week). Subjects were recruited via advertisement displayed on the website of the University of Basel. Mainly university students were included. Screening visits and sessions were performed in the Ambulatory Study Center, located in the Department of Clinical Research at the University Hospital of Basel.

Screening procedure: Subjects were examined by a study physician. Basic health was ensured by general medical examination including medical history, physical examination, electrocardiogram, determination of body weight and blood chemistry and haematology analysis. Additionally, subjects were screened using a semi-structured clinical interview for DSM-V (Wittchen et al., 1997) to exclude those with a personal or first-degree relative axis I major psychiatric disorder (acute or past) or a history of drug dependence. Additionally, the 'Self-screening Prodrome' (Kammermann et al., 2009) was used to ensure early detection of psychotic tendencies. Axis I major psychiatric disorders also include addiction disorders.

Informed consent: Subjects were informed about the study procedures and associated risks in advance through the written participant information.

Study Procedures:

Psychometric Assessments:

Subjective Effects Questionnaire (Visual Analog Scales, VAS): VAS were repeatedly used to assess subjective alterations in consciousness over time. Single scales were presented as 100 mm horizontal lines marked with "not at all" on the left and "extremely" on the right. The following VAS items were used: "any drug effect", "good drug effect", "bad drug effect", "high", "anxiety", "nausea", "alteration of vision", "sounds seem to influence what I see", "alteration of sense of time", "the boundaries between myself and my surroundings seem to blur", "I am emotional", "talkative", "open", "trust", and "my focus is directed inward/outward". Scales were administered before and repeatedly after substance administration.

Figure 6A:
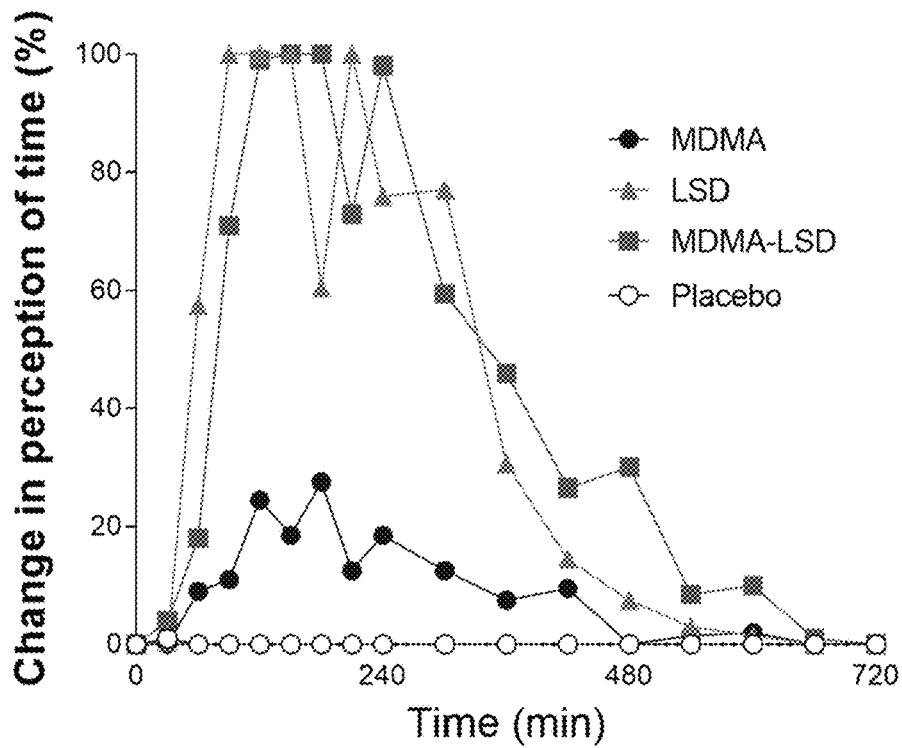
FIG. 6A is a graph showing change in perception of time and FIG. 6B is a graph showing ego-dissolution.
Figure 6B:
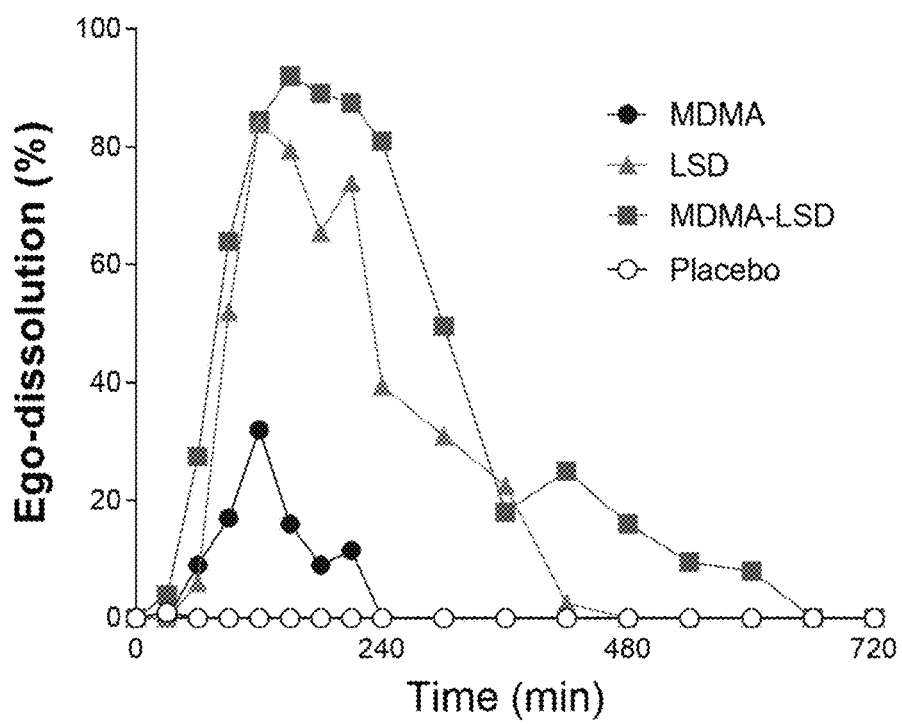

5-Dimensional Altered States of Consciousness (5D-ASC): The 5-dimensional Altered States of Consciousness (5D-ASC) Scale is a visual analog scale consisting of 94 items (Dittrich, 1998; Studerus et al., 2010). The instrument contains five main scales and 11 newer subscales assessing mood, anxiety, derealization, depersonalization, changes in perception, auditory alterations, and reduced vigilance. The scale is well-validated (Studerus et al., 2010). The 5D-ASC scale was administered once at the end of the session and subjects were instructed to retrospectively rate peak alterations that have been experienced during the study session. Each item of the scale is scored on a 0-100 mm VAS. The attribution of the individual items to the subscales of the 5D-ASC was analyzed according to (Dittrich, 1998; Studerus et al., 2010) and as shown in FIGS. 6A-6B. The scale was administered once at the end of each test session.

Autonomic measures: Blood pressure, heart rate, and body temperature were recorded at baseline and repeatedly throughout the session. Blood pressure (systolic and diastolic) and heart rate were measured with an automatic oscillometric device. Body temperature was measured with an ear thermometer.

Adverse effects (list of complaints): The list of complaints (LC) consists of 66 items offering a global score measuring physical and general discomfort (Zerssen, 1976). The LC list was administered at the end of the session with reference to complaints throughout the entire session.

The study included additional outcomes not discussed here.

Substance preparation and quality control: MDMA was prepared as capsules containing 25 mg of analytically pure MDMA hydrochloride and mannitol filler. The dose of 100 mg of MDMA consisted of four capsules of 25 mg. LSD was prepared as an oral solution containing 100 µg of analytically pure LSD (Lipomed AG, Arlesheim, Switzerland) in 1 ml of ethanol. All substance formulations plus matching placebos were prepared by a GMP facility (Apotheke Dr. Hysek, Biel, Switzerland) according to GMP guidelines. LSD-placebo solutions consisted of only ethanol, MDMA-placebo capsules consisted of only mannitol. All placebos were prepared by the same GMP facility and looked identical to the *verum* preparations to ensure proper blinding. The study used a double-dummy design. Subjects received an LSD *verum* with an MDMA *verum*, an LSD placebo with an MDMA *verum*, an LSD *verum* with an MDMA placebo, or an LSD placebo with an MDMA placebo on each of the four study days. Randomization, packaging, labelling, and quality control (QC) including stability tests were handled by the GMP facility. Subjects and study personnel involved in supervising the session were blinded to treatment order that was balanced.

Results of the Clinical Study

Example data taken from the clinical study are shown. Data are the mean values observed in a sample of two healthy human subjects who completed the entire study and were each administered with all four treatment conditions allowing for a direct within-subject comparison of the effects of LSD alone, MDMA alone and MDMA and LSD together.

Acute Effects on VAS

Figure 2A:
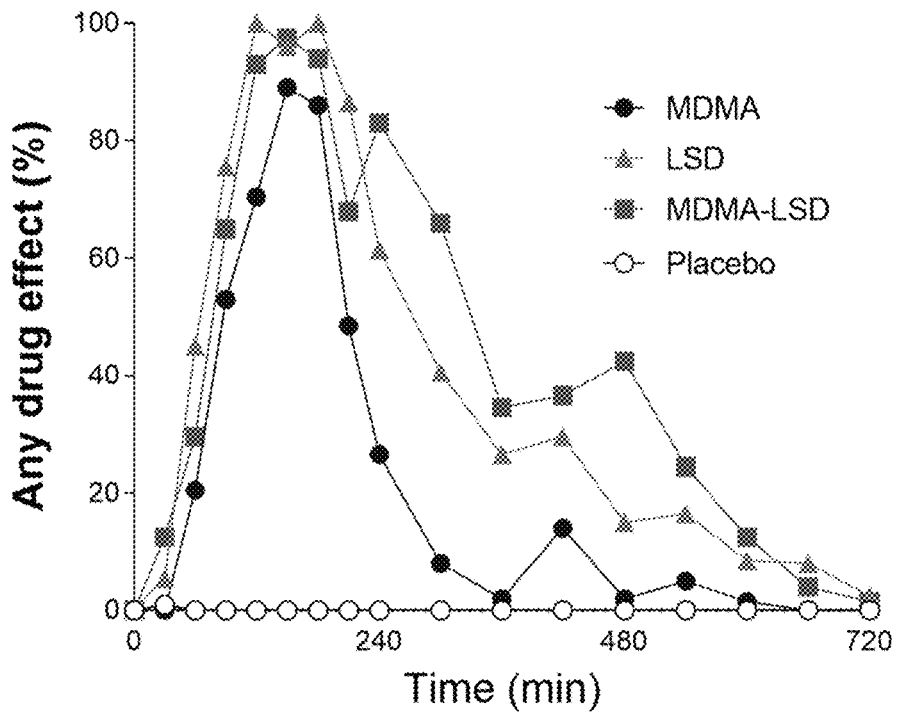
FIG. 2A is a graph showing any drug effects and FIG. 2B is a graph showing good drug effects.

MDMA, LSD and MDMA-LSD produced comparable peak subjective effects ratings of any drug effect. As expected, effects of LSD lasted longer than those of MDMA. The MDMA-LSD effect lasted equally long or slightly longer than the effect of LSD alone (FIG. 2A).

Figure 2B:
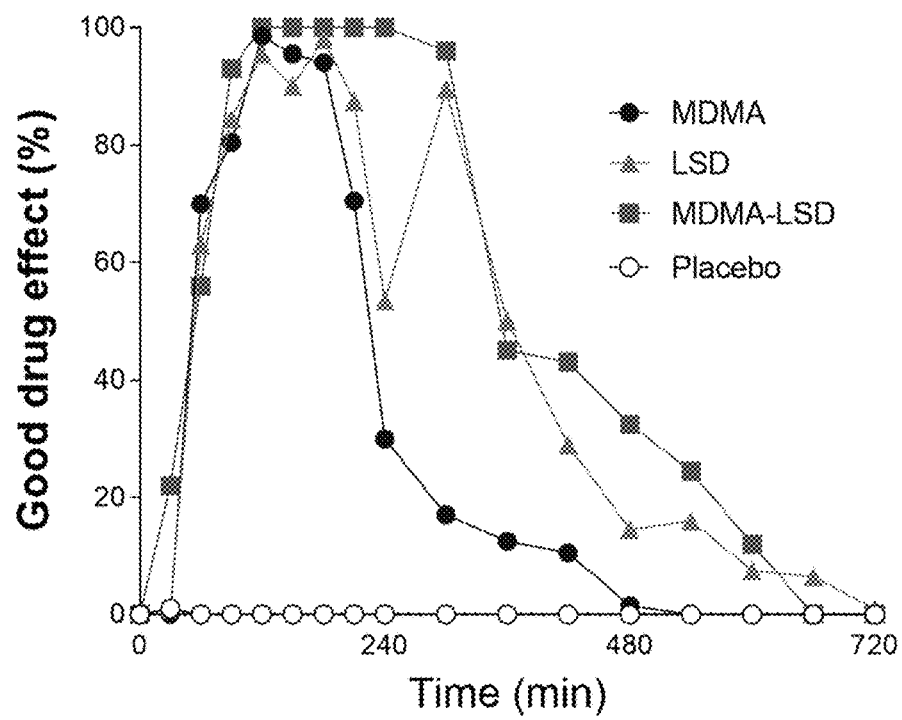

All active treatments produced good drug effects of similar intensity. However, good drug effects lasted longer after LSD and remained highest after MDMA-LSD. Thus, the most stable and prolonged good drug response was observed after MDMA-LSD (FIG. 2B).

Figure 3A:
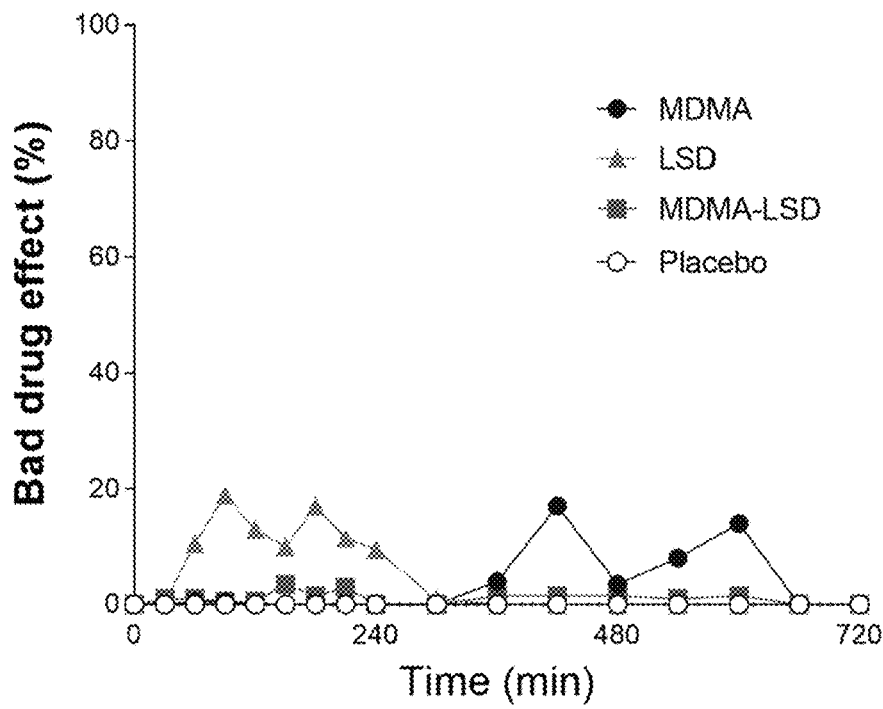
FIG. 3A is a graph showing bad drug effects and FIG. 3B is a graph showing anxiety.
Figure 3B:
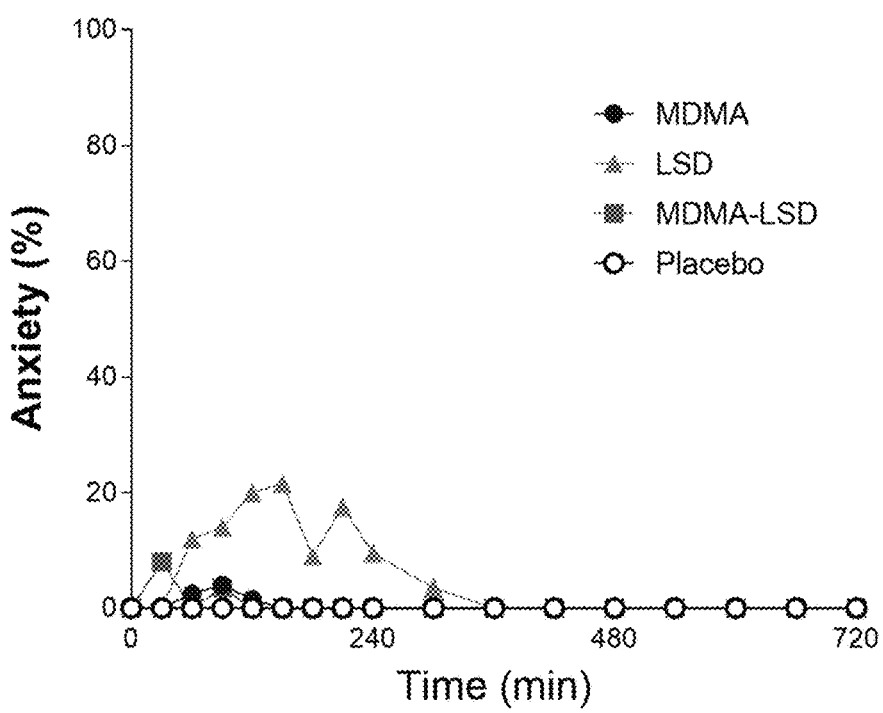

LSD produced minor subjective bad drug effects and anxiety at effect onset and up to 240 minutes after administration. MDMA alone also moderately increased subjective bad drug effect ratings, however, this was after the acute drug effect 300-660 minutes after administration. Importantly, no bad drug effects were reported after MDMA-LSD (FIG. 3A). Thus, MDMA reduced LSD-associated bad drug effects. Similarly, LSD produced moderate anxiety at drug effect onset and this effect was reduced by MDMA resulting in no relevant anxiety in the MDMA-LSD condition (FIG. 3B).

Figure 4A:
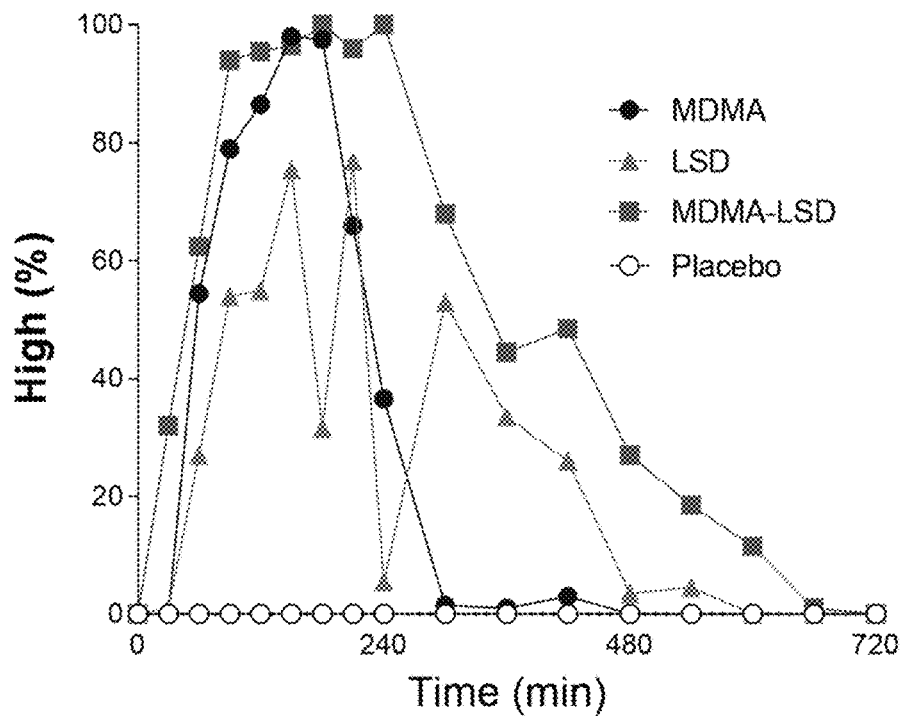
FIG. 4A is a graph showing subjective drug high effects and FIG. 4B is a graph showing nausea.
Figure 4B:
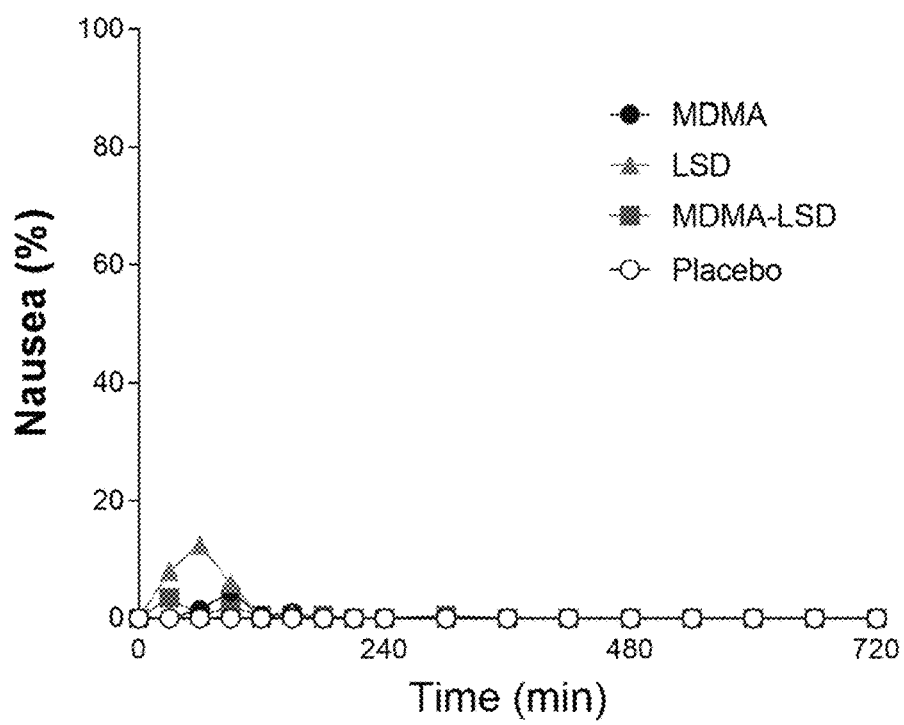

The combination of MDMA and LSD induced a more robust and longer-lasting self-reported feeling of high compared with MDMA or LSD alone (FIG. 4A). LSD induced moderate nausea at drug effect onset but only when given alone (FIG. 4B).

Figure 5A:
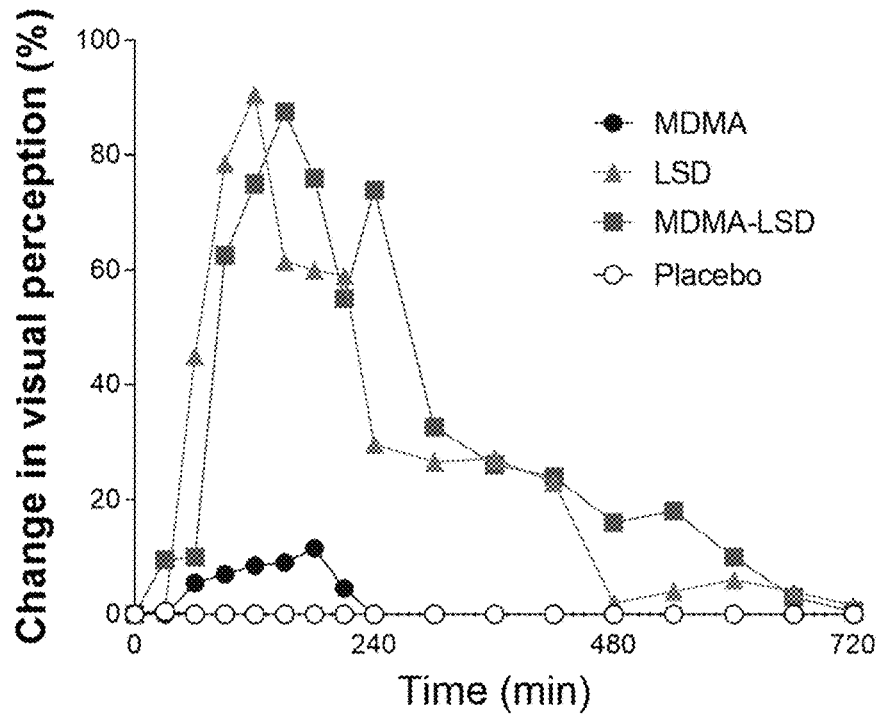
FIG. 5A is a graph showing changes in visual perception and FIG. 5B is a graph showing synaesthesias (sounds influenced visual perception)
Figure 5B:
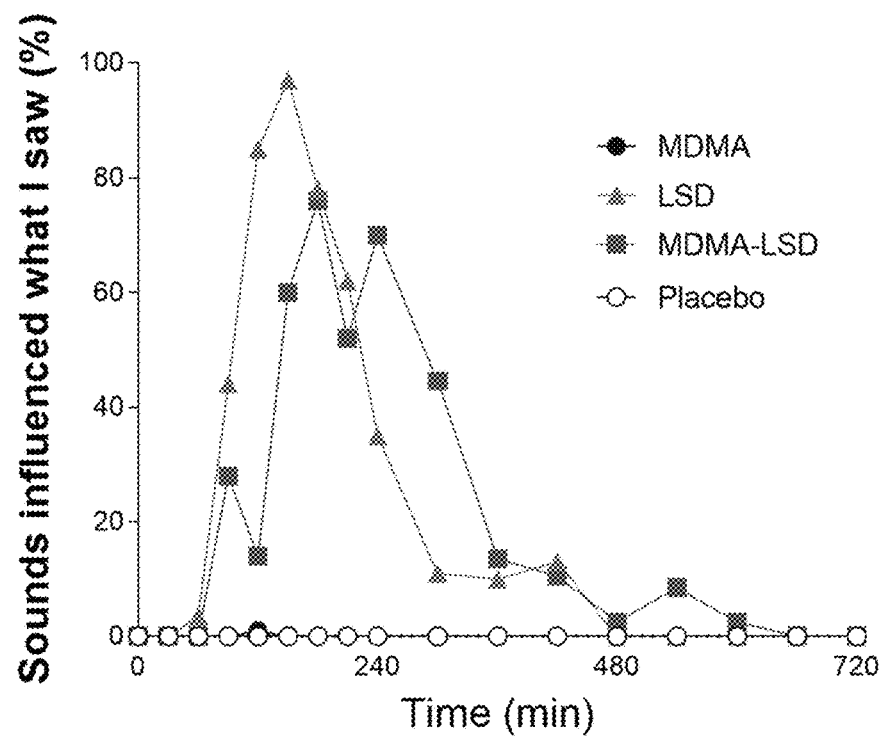

LSD and MDMA-LSD induced comparable changes in visual perception (FIG. 5A) and synaesthesias (sounds influencing visual perception) (FIG. 5B).

LSD and MDMA-LSD induced comparable changes in the perception of time and similar experiences of ego-dissolution, possibly being more robust and lasting longer after MDMA-LSD compared with LSD alone (FIGS. 6A and 6B).

Figure 7A:
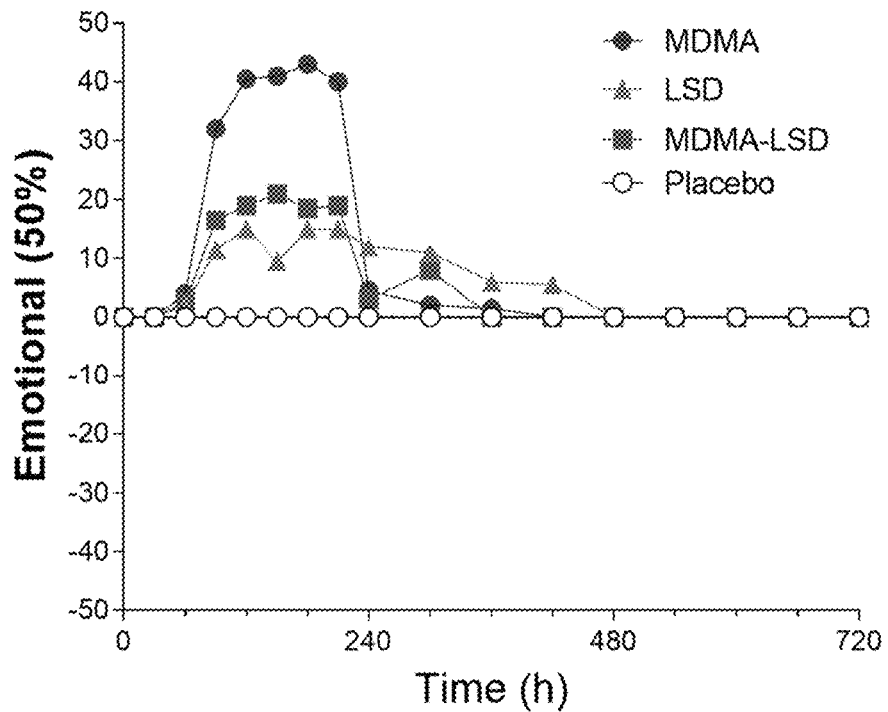
FIG. 7A is a graph showing effects on subjective feelings of being emotional and FIG. 7B is a graph showing effects on subjective feelings of being happy.
Figure 7B:
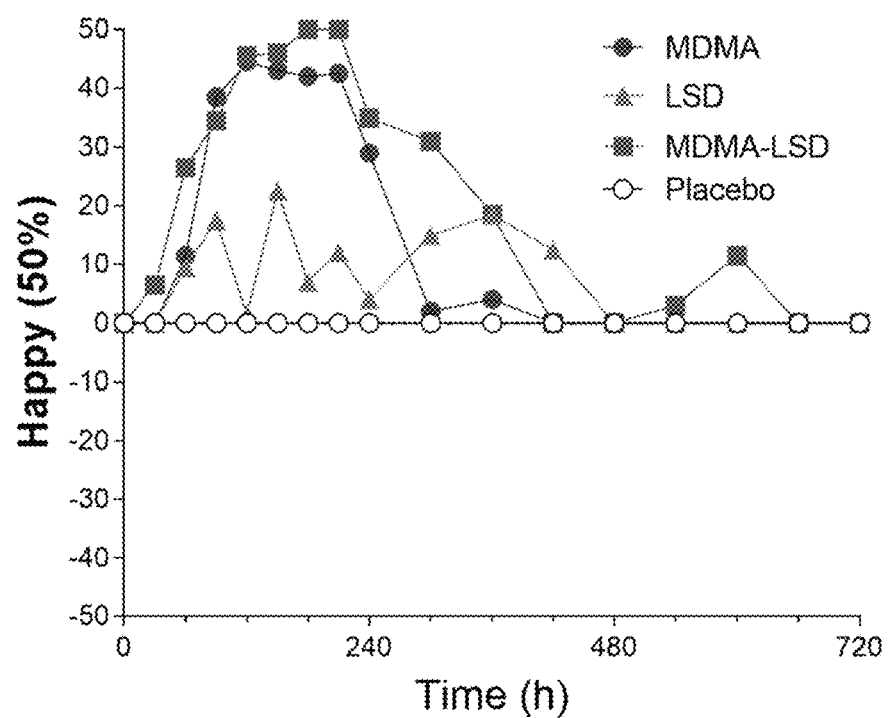

MDMA typically induces feelings of being more emotional and feelings of happiness. When combined with MDMA, LSD produced slightly greater feelings of emotionality (FIG. 7A) and significantly greater happiness (FIG. 7B) compared to LSD alone.

Figure 8A:
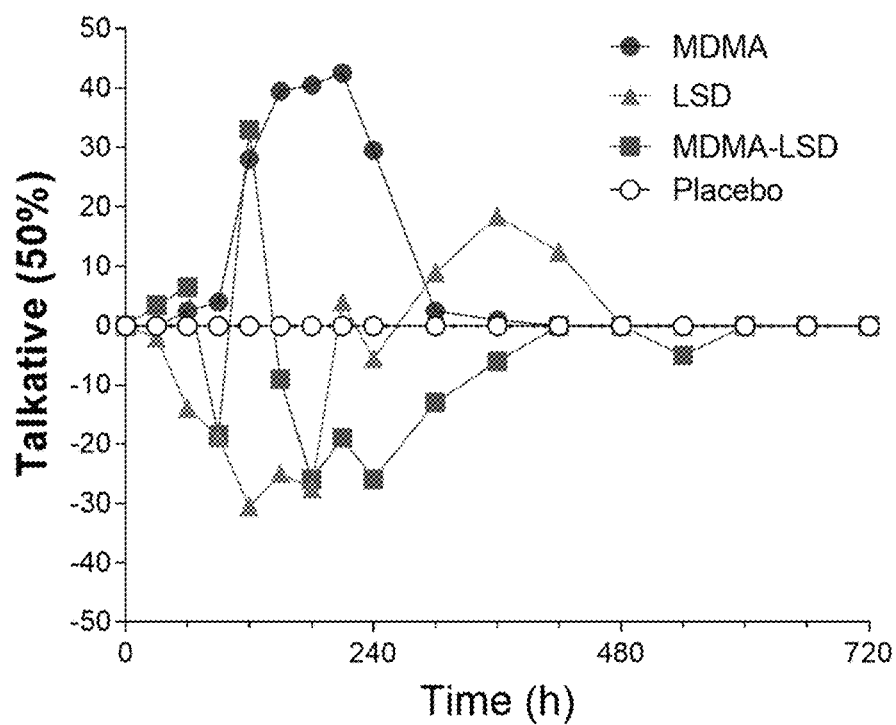
FIG. 8A is a graph showing effects on being talkative and FIG. 8B is a graph showing effects on being open.
Figure 8B:
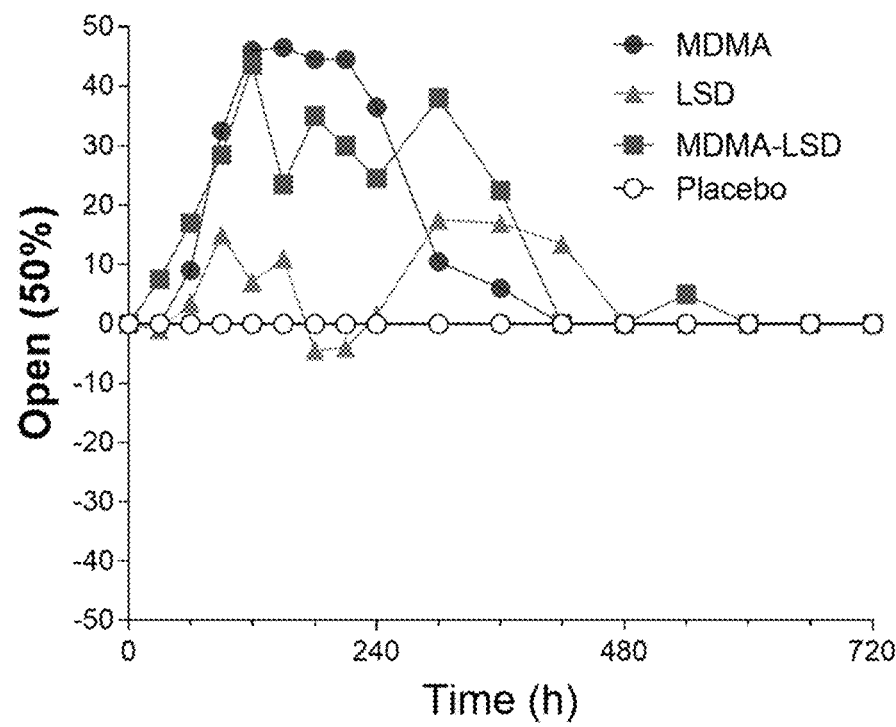

As shown in FIG. 8A, MDMA increases ratings of being talkative and LSD reduces talkative especially during the first 240 minutes after administration. When combined these opposite effects of the single substances are less prominent (FIG. 8A).

MDMA increases ratings of openness. This is also the case when MDMA is given with LSD while LSD along produces lower increases in openness (FIG. 8A). Thus, the LSD experience becomes more MDMA-like and more empathogenic when combined with MDMA.

Figure 9A:
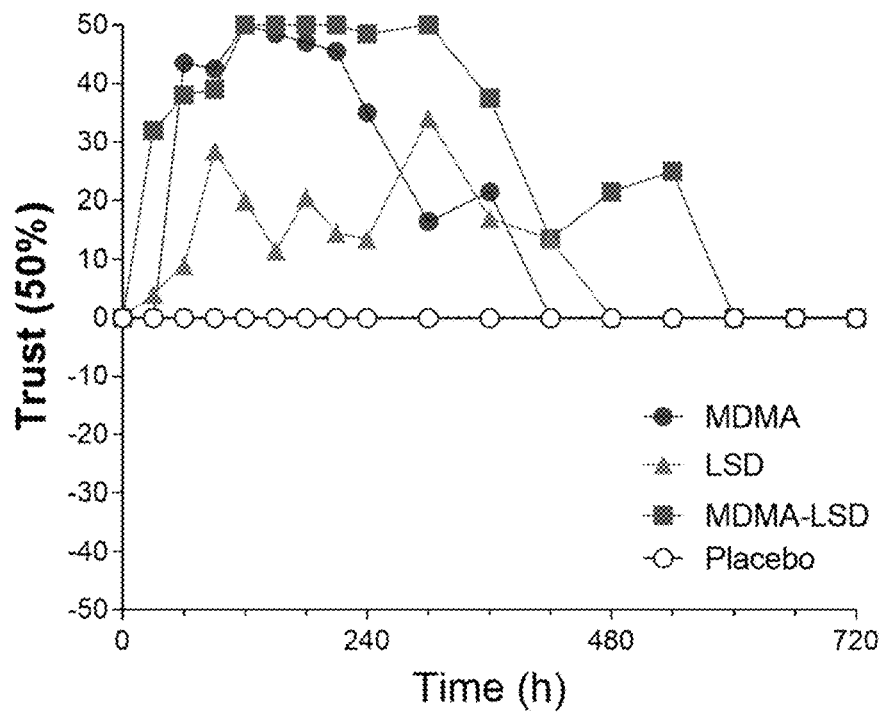
FIG. 9A is a graph showing effects on ratings of trust and FIG. 9B is a graph showing effects on ratings of feeling close.
Figure 9B:
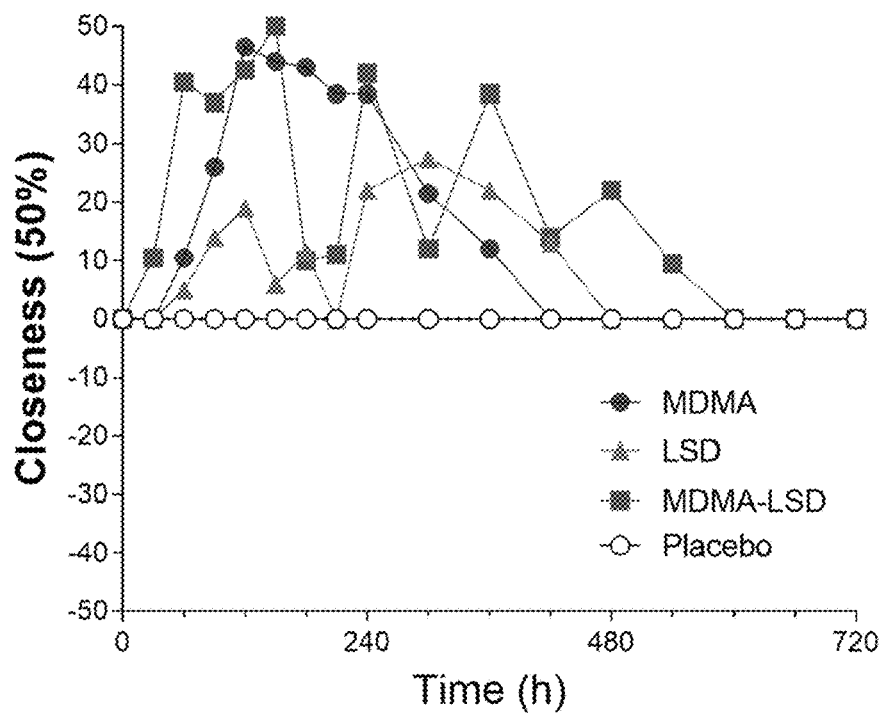

MDMA increases feelings of trust and openness (FIGS. 9A and 9B). MDMA-LSD produced greater ratings of trust and openness compared with LSD alone (FIGS. 9A and 9B).

Figure 10A:
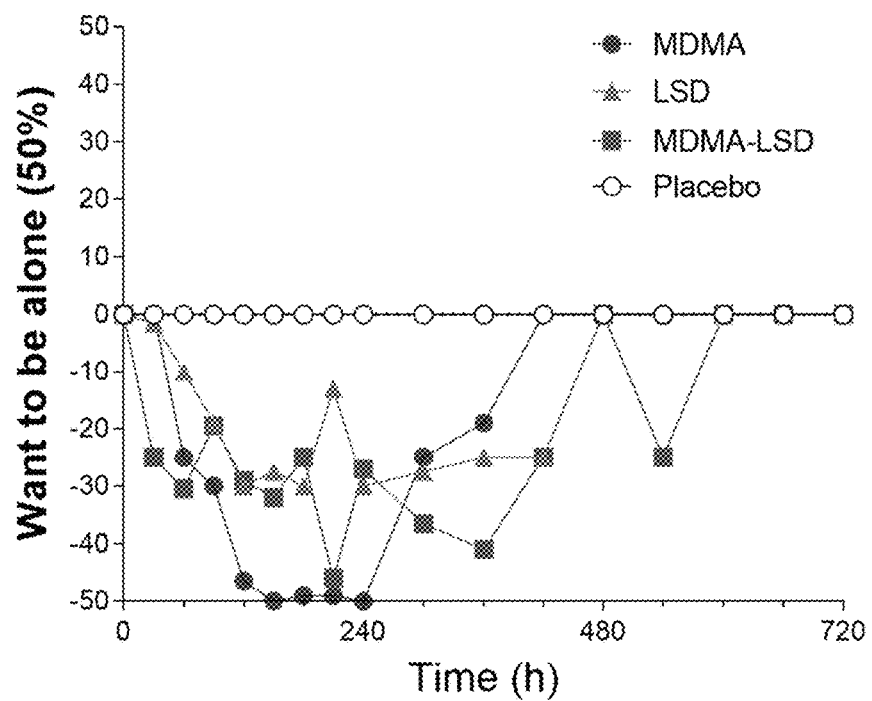
FIG. 10A is a graph showing subjects ratings of wanting to be alone and FIG. 10B is a graph showing subjects ratings of wanting to be with other people.
Figure 10B:
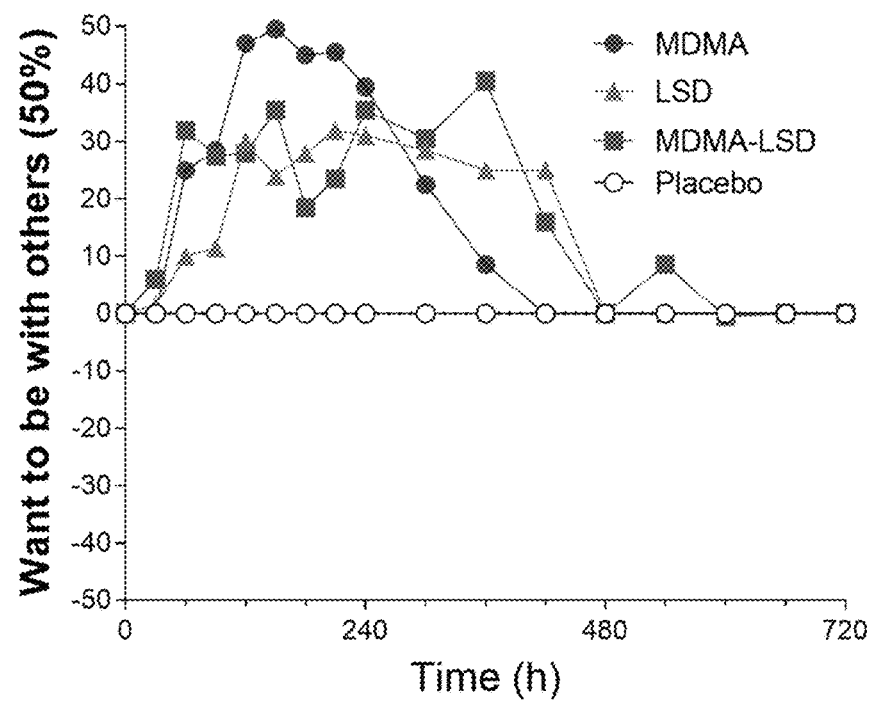

After MDMA or LSD or MDMA-LSD administration subjects wanted to be with others and not alone. This effect was comparable across drug conditions (FIGS. 10A and 10B).

Figure 11:
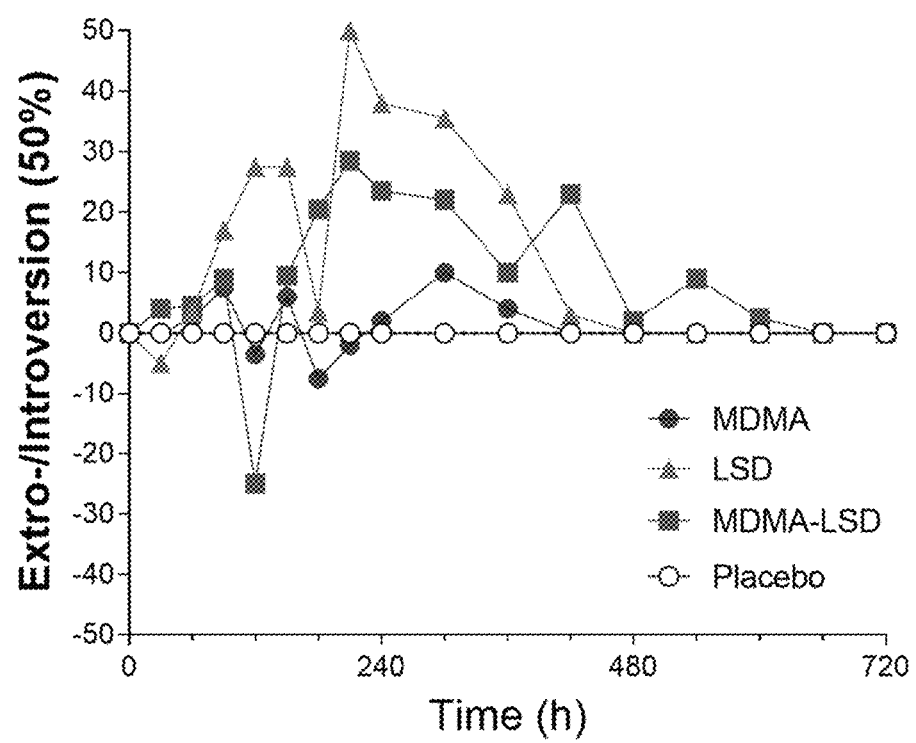
FIG. 11 is a graph showing ratings of extro-/introversion.

LSD alone had no effect on the degree of intro or extroversion. MDMA-LSD produced greater extroversion compared with LSD alone (FIG. 11).

Acute Effects on 5D-ASD

Figure 12:
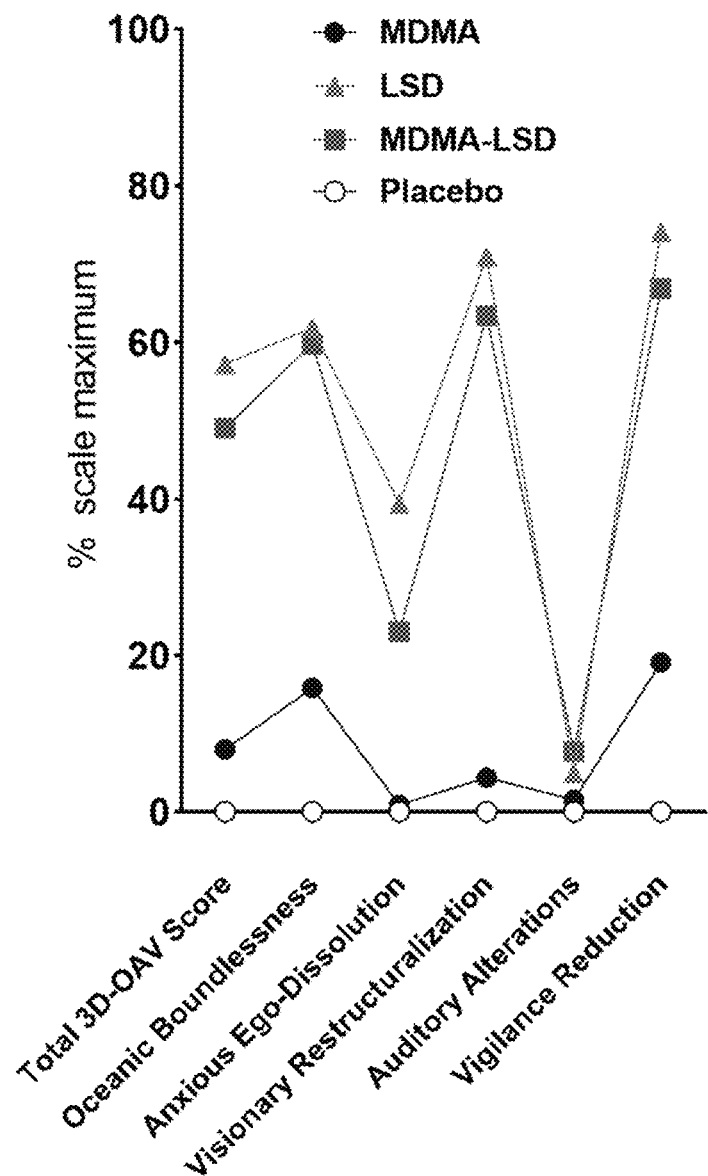
FIG. 12 is a graph showing 5D-ASC main scale score ratings.
Figure 13:
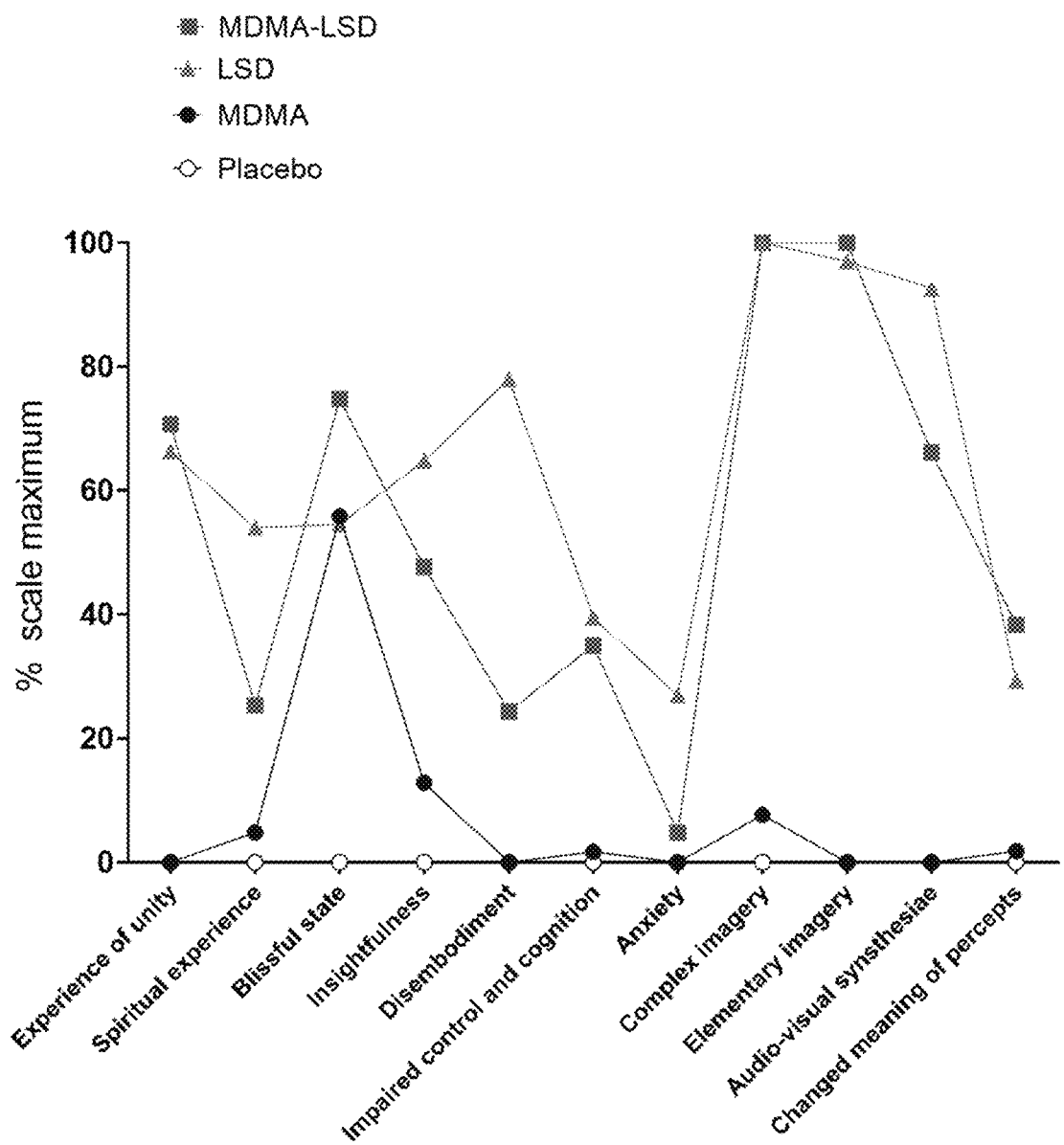
FIG. 13 is a graph showing 5D-ASC subscale ratings.

LSD and MDMA-LSD induced comparable degrees of alterations of consciousness on the 5D-ASC main (FIG. 12) and subscales (FIG. 13). Importantly, feelings of bliss tended to be greater after MDMA-LSD compared with LSD alone (FIG. 13). Consistently, negative effects of LSD including disembodiment and anxiety were reduced by MDMA co-administration (FIG. 13).

Vital Signs

Figure 14A:
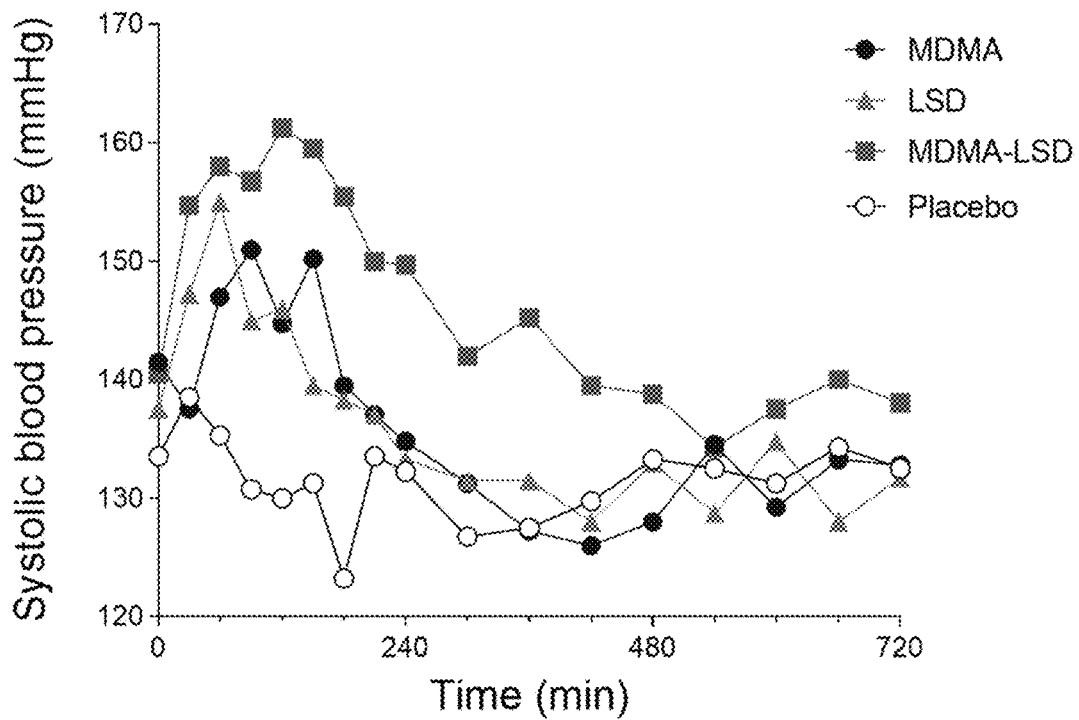
FIG. 14A is a graph showing systolic blood pressure and FIG. 14B is a graph showing diastolic blood pressure.
Figure 14B:
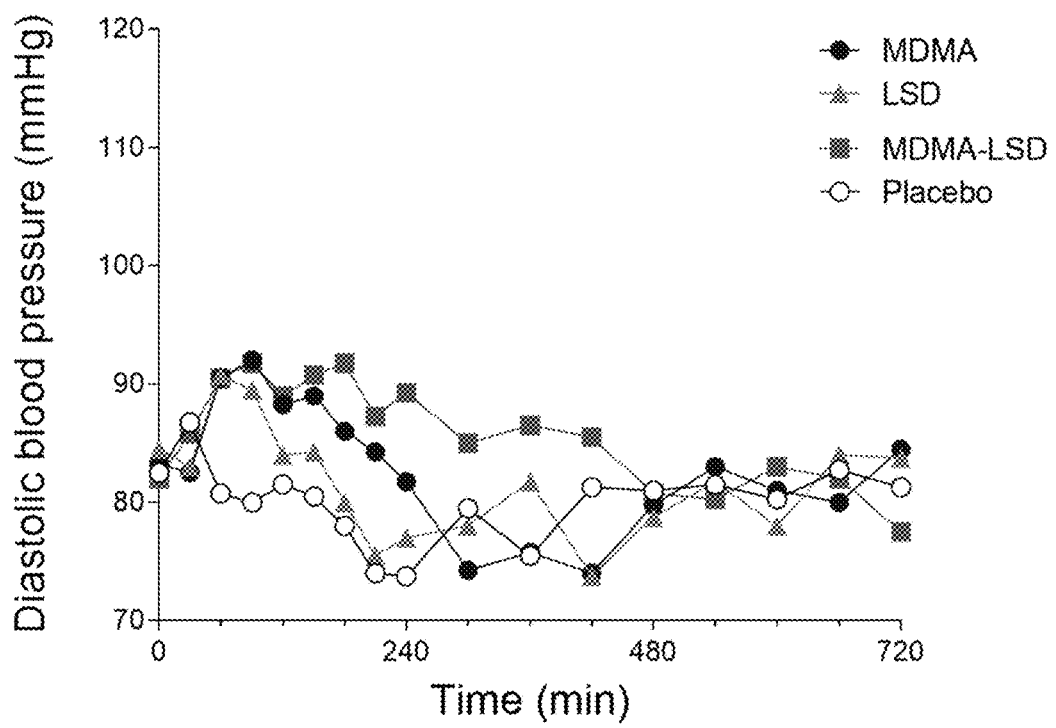
Figure 15A:
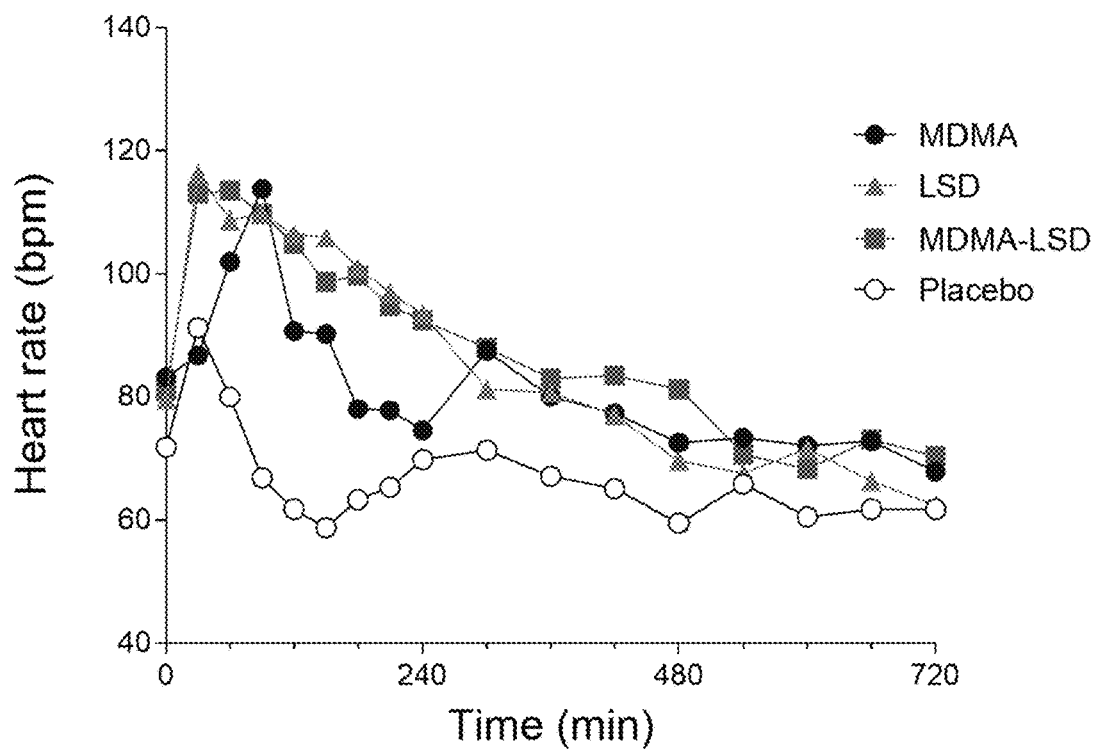
FIG. 15A is a graph showing heart rate and FIG. 15B is a graph showing body temperature.
Figure 15B:
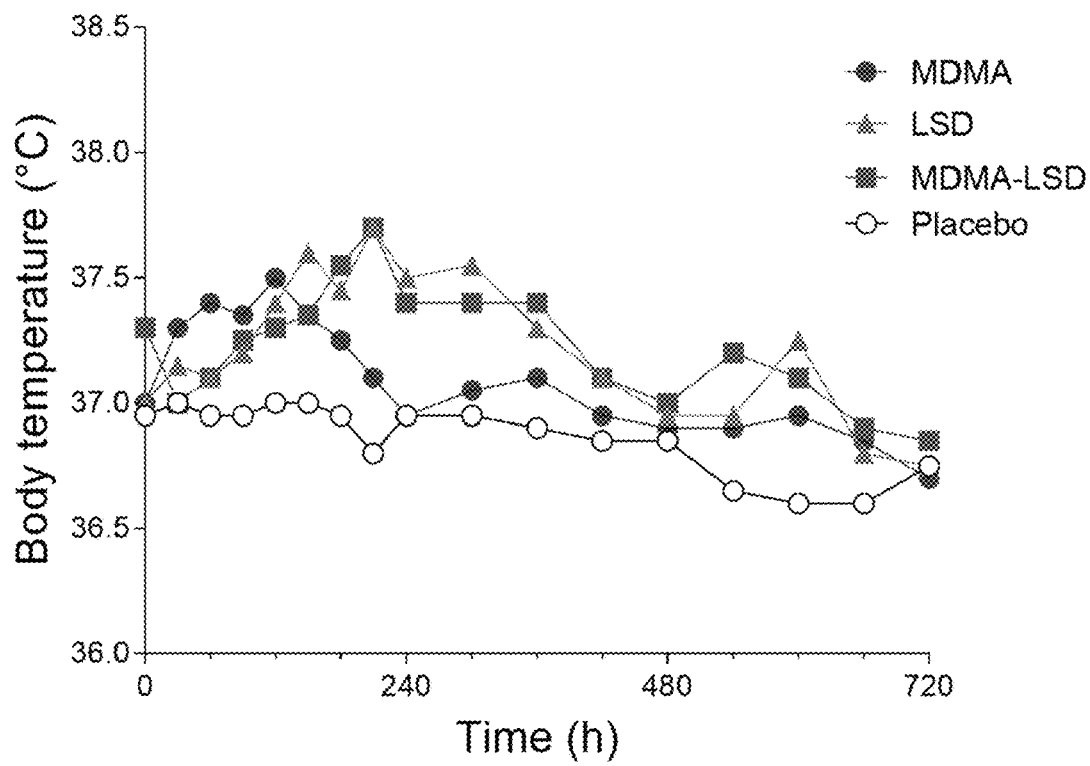

MDMA-LSD increased systolic and diastolic blood pressure slightly more and for a longer time than MDMA or LSD alone (FIGS. 14A and 14B). MDMA-LSD produced comparable effects on heart rate and body temperature to LSD alone (FIGS. 15A and 15B).

Adverse Effects (LC Score)

Total average LC scores were increased by placebo, MDMA, LSD, and MDMA-LSD to 5, 12, 18, and 12, respectively. Thus, MDMA-LSD produce a lower mean number of acute complaints compared with LSD alone.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Barrett F S, Preller K H, Herdener M, Janata P, Vollenweider F X (2018). Serotonin 2A Receptor Signaling Underlies LSD-induced Alteration of the Neural Response to Dynamic Changes in Music. *Cereb Cortex* 28: 3939-3950.
2. Bershad A K, Miller M A, Baggott M J, de Wit H (2016a). The effects of MDMA on socio-emotional processing: does MDMA differ from other stimulants? *J Psychopharmacol* 30: 1248-1258.
3. Bershad A K, Weafer J J, Kirkpatrick M G, Wardle M C, Miller M A, de Wit H (2016b). Oxytocin receptor gene variation predicts subjective responses to MDMA. *Soc Neurosci* 11: 592-599.
4. Carhart-Harris R L, Kaelen M, Bolstridge M, Williams T M, Williams L T, Underwood R, et al. (2016). The paradoxical psychological effects of lysergic acid diethylamide (LSD). *Psychol Med* 46: 1379-1390.
5. Dittrich A (1998). The standardized psychometric assessment of altered states of consciousness (ASCs) in humans. Pharmacopsychiatry 31 (Suppl 2): 80-84.
6. Dolder P C, Schmid Y, Mueller F, Borgwardt S, Liechti M E (2016). LSD acutely impairs fear recognition and enhances emotional empathy and sociality. *Neuropsychopharmacology* 41: 2638-2646.
7. Dolder P C, Muller F, Schmid Y, Borgwardt S J, Liechti M E (2018). Direct comparison of the acute subjective, emotional, autonomic, and endocrine effects of MDMA, methylphenidate, and modafinil in healthy subjects. *Psychopharmacology* 235: 467-479.
8. Dolder P C, Schmid Y, Steuer A E, Kraemer T, Rentsch K M, Hammann F, et al. (2017). Pharmacokinetics and pharmacodynamics of lysergic acid diethylamide in healthy subjects. *Clin Pharmacokinetics* 56: 1219-1230.
9. Farre M, Abanades S, Roset P N, Peiro A M, Torrens M, O'Mathuna B, et al. (2007). Pharmacological interaction between 3,4-methylenedioxymethamphetamine (ecstasy) and paroxetine: pharmacological effects and pharmacokinetics. *J Pharmacol Exp Ther* 323: 954-962.
10. Gallimore A R, Strassman R J (2016). A model for the application of target-controlled intravenous infusion for prolonged immersive DMT psychedelic experience. *Front Pharmacol* doi: 10.3389/fphar.2016.00211.
11. Garcia-Romeu A, Griffiths R R, Johnson M W (2015). Psilocybin-occasioned mystical experiences in the treatment of tobacco addiction. *Curr Drug Abuse Rev* 7: 157-164.
12. Griffiths R, Richards W, Johnson M, McCann U, Jesse R (2008). Mystical-type experiences occasioned by psilocybin mediate the attribution of personal meaning and spiritual significance 14 months later. *J Psychopharmacol* 22: 621-632.
13. Griffiths R R, Johnson M W, Carducci M A, Umbricht A, Richards W A, Richards B D, et al. (2016). Psilocybin produces substantial and sustained decreases in depression and anxiety in patients with life-threatening cancer: a randomized double-blind trial. *J Psychopharmacol* 30: 1181-1197.
14. Hasler F, Grimberg U, Benz M A, Huber T, Vollenweider F X (2004). Acute psychological and physiological effects of psilocybin in healthy humans: a double-blind, placebo-controlled dose-effect study. *Psychopharmacology* 172: 145-156.
15. Hintzen A, Passie T (2010). *The pharmacology of LSD: a critical review*. edn. Oxford University Press: Oxford.
16. Holze F, Duthaler U, Vizeli P, Muller F, Borgwardt S, Liechti M E (2019a). Pharmacokinetics and subjective effects of a novel oral LSD formulation in healthy subjects. *Br J Clin Pharmacol* 85: 1474-1483.
17. Holze F, Vizeli P, Muller F, Ley L, Duerig R, Varghese N, et al. (2019b). Distinct acute effects of LSD, MDMA, and D-amphetamine in healthy subjects. *Neuropsychopharmacology*.
18. Hysek C M, Simmler L D, Ineichen M, Grouzmann E, Hoener M C, Brenneisen R, et al. (2011). The norepinephrine transporter inhibitor reboxetine reduces stimulant effects of MDMA ("ecstasy") in humans. *Clinical pharmacology and therapeutics* 90: 246-255.
19. Hysek C M, Simmler L D, Schillinger N, Meyer N, Schmid Y, Donzelli M, et al. (2014a). Pharmacokinetic and pharmacodynamic effects of methylphenidate and MDMA administered alone and in combination. *Int J Neuropsychopharmacol* 17: 371-381.
20. Hysek C M, Simmler L D, Nicola V, Vischer N, Donzelli M, Krähenbühl S, et al. (2012). Duloxetine inhibits effects of MDMA ("ecstasy") in vitro and in humans in a randomized placebo-controlled laboratory study. *PLoS One* 7: e36476.
21. Hysek C M, Schmid Y, Simmler L D, Domes G, Heinrichs M, Eisenegger C, et al. (2014b). MDMA enhances emotional empathy and prosocial behavior. *Soc Cogn Affect Neurosci* 9: 1645-1652.
22. Kammermann J, Stieglitz R D, & Riecher-Rossler A (2009). Self-screen prodrome"—self-rating for the early detection of mental disorders and psychoses. *Fortschr Neurol Psychiatr* 77: 278-284.
23. Kirkpatrick M G, Francis S M, Lee R, de Wit H, Jacob S (2014). Plasma oxytocin concentrations following MDMA or intranasal oxytocin in humans. *Psychoneuroendocrinology* 46: 23-31.
24. Kraehenmann R, Pokorny D, Vollenweider L, Preller K H, Pokorny T, Seifritz E, et al. (2017). Dreamlike effects of LSD on waking imagery in humans depend on serotonin 2A receptor activation. *Psychopharmacology* 234: 2031-2046.
25. Liechti M E (2017). Modern clinical research on LSD. *Neuropsychopharmacology* 42: 2114-2127.
26. Liechti M E, Vollenweider F X (2000a). The serotonin uptake inhibitor citalopram reduces acute cardiovascular and vegetative effects of 3,4-methylenedioxymethamphetamine ('Ecstasy') in healthy volunteers. *J Psychopharmacol* 14: 269-274.
27. Liechti M E, Vollenweider F X (2001). Which neuroreceptors mediate the subjective effects of MDMA in humans? A summary of mechanistic studies. *Human psychopharmacology* 16: 589-598.
28. Liechti M E, Baumann C, Gamma A, Vollenweider F X (2000b). Acute psychological effects of 3,4-methylenedioxymethamphetamine (MDMA, "Ecstasy") are attenuated by the serotonin uptake inhibitor citalopram. *Neuropsychopharmacology* 22: 513-521.
29. Liechti M E, Saur M R, Gamma A, Hell D, Vollenweider F X (2000c). Psychological and physiological effects of MDMA ("Ecstasy") after pretreatment with the 5-HT(2) antagonist ketanserin in healthy humans. *Neuropsychopharmacology* 23: 396-404.
30. Marona-Lewicka D, Nichols D E (2007). Further evidence that the delayed temporal dopaminergic effects of LSD are mediated by a mechanism different than the first temporal phase of action. *Pharmacology, biochemistry, and behavior* 87: 453-461.
31. Marona-Lewicka D, Thisted R A, Nichols D E (2005). Distinct temporal phases in the behavioral pharmacology of LSD: dopamine D2 receptor-mediated effects in the rat and implications for psychosis. *Psychopharmacology* 180: 427-435.
32. Mittman S M, Geyer M A (1991). Dissociation of multiple effects of acute LSD on exploratory behavior in rats by ritanserin and propranolol. *Psychopharmacology* 105: 69-76.
33. Nichols D E (2016). *Psychedelics. Pharmacological reviews* 68: 264-355.
34. Nichols D E, Grob C S (2018). Is LSD toxic? *Forensic science international* 284: 141-145.
35. Passie T, Halpern J H, Stichtenoth D O, Emrich H M, Hintzen A (2008). The pharmacology of lysergic acid diethylamide: a review. *CNS Neurosci Ther* 14: 295-314.
36. Preller K H, Herdener M, Pokorny T, Planzer A, Kraehenmann R, Stämpfli P, et al. (2017). The fabric of meaning and subjective effects in LSD-induced states depend on serotonin 2A receptor activation *Curr Biol* 27: 451-457.
37. Ramos L, Hicks C, Caminer A, Couto K, Narlawar R, Kassiou M, et al. (2016). MDMA ('Ecstasy'), oxytocin and vasopressin modulate social preference in rats: A role for handling and oxytocin receptors. *Pharmacology, biochemistry, and behavior* 150-151: 115-123.

38. Rickli A, Moning O D, Hoener M C, Liechti M E (2016). Receptor interaction profiles of novel psychoactive tryptamines compared with classic hallucinogens. *European neuropsychopharmacology: the journal of the European College of Neuropsychopharmacology* 26: 1327-1337.
39. Roseman L, Nutt D J, Carhart-Harris R L (2017). Quality of acute psychedelic experience predicts therapeutic efficacy of psilocybin for treatment-resistant depression. *Front Pharmacol* 8: 974.
40. Ross S, Bossis A, Guss J, Agin-Liebes G, Malone T, Cohen B, et al. (2016). Rapid and sustained symptom reduction following psilocybin treatment for anxiety and depression in patients with life-threatening cancer: a randomized controlled trial. *J Psychopharmacol* 30: 1165-1180.
41. Schmid Y, Liechti M E (2018). Long-lasting subjective effects of LSD in normal subjects. *Psychopharmacology* 235: 535-545.
42. Schmid Y, Hysek C M, Simmler L D, Crockett M J, Quednow B B, Liechti M E (2014). Differential effects of MDMA and methylphenidate on social cognition. *J Psychopharmacol* 28: 847-856.
43. Schmid Y, Enzler F, Gasser P, Grouzmann E, Preller K H, Vollenweider F X, et al. (2015). Acute effects of lysergic acid diethylamide in healthy subjects. *Biol Psychiatry* 78: 544-553.
44. Simmler L, Buser T, Donzelli M, Schramm Y, Dieu L H, Huwyler J, et al. (2013). Pharmacological characterization of designer cathinones in vitro. *Br J Pharmacol* 168: 458-470.
45. Strassman R J (1996). Human psychopharmacology of N,N-dimethyltryptamine. *Behav Brain Res* 73: 121-124.
46. Strassman R J, Qualls C R (1994a). Dose-response study of N,N-dimethyltryptamine in humans: I. Neuroendocrine, autonomic, and cardiovascular effects. *Archives of general psychiatry* 51: 85-97.
47. Strassman R J, Qualls C R, Uhlenhuth E H, Kellner R (1994b). Dose-response study of N,N-dimethyltryptamine in humans: II. Subjective effects and preliminary results of a new rating scale. *Archives of general psychiatry* 51: 98-108.
48. Studerus E, Gamma A, Kometer M, Vollenweider F X (2012). Prediction of psilocybin response in healthy volunteers. *PLoS One* 7: e30800.
49. Tancer M, Johanson C E (2003). Reinforcing, subjective, and physiological effects of MDMA in humans: a comparison with d-amphetamine and mCPP. *Drug and alcohol dependence* 72: 33-44.
50. Timmermann C, Roseman L, Schartner M, Milliere R, Williams L T J, Erritzoe D, et al. (2019). Neural correlates of the DMT experience assessed with multivariate EEG. *Sci Rep* 9: 16324.
51. Verrico C D, Miller G M, Madras B K (2007). MDMA (ecstasy) and human dopamine, norepinephrine, and serotonin transporters: implications for MDMA-induced neurotoxicity and treatment. *Psychopharmacology* 189: 489-503.
52. Vizeli P, Liechti M E (2017). Safety pharmacology of acute MDMA administration in healthy subjects. *J Psychopharmacol* 31: 576-588.
53. Vizeli P, Liechti M E (2018). Oxytocin receptor gene variations and socio-emotional effects of MDMA: A pooled analysis of controlled studies in healthy subjects. *PLoS One* 13: e0199384.
54. Wittchen H U, Wunderlich U, Gruschwitz S, & Zaudig M (1997) *SKID-I: Strukturiertes Klinisches Interview für DSM-IV*. Hogrefe-Verlag: Göttingen.
55. Zerssen D V (1976) *Die Beschwerden-Liste. Münchener Informationssystem*. Psychis: München.

What is claimed is:

1. A method of treating a psychiatric disorder that affects mood including the step of:
administering a synergistic amount of 3,4-methylenedioxymethamphetamine (MDMA) in combination with a synergistic amount of LSD together in a single dosage form to a human individual, wherein MDMA is administered in a dose of 20-200 mg and LSD is administered in a dose of 0.05-0.3 mg, wherein said administration enhances a mood of the patient prior to administration of the psychedelic and improves good drug effects of blissful state and feeling open and reduces bad drug effects of anxiety as measured with psychometric assessments of Subjective Effects Questionnaire (Visual Analog Scales (VAS)) and 5-Dimensional Altered States of Consciousness ((5D-ASC), and wherein the MDMA enhances a positive over negative mood effect profile of the LSD in the individual; and
treating the psychiatric disorder that affects mood chosen from the group consisting of depression and anxiety.

2. The method of claim 1, wherein the MDMA and LSD have different release profiles.

3. The method of claim 1, wherein the MDMA reduces anxiety up to 6 hours after administration.

4. The method of claim 1,
wherein said administration induces the release of endogenous monoamines, and stimulates $5\text{-HT}_{2A}$ receptors, and wherein said administration step improves good drug effects of blissful state and feeling open and reduces bad drug effects of anxiety in the individual as measured with psychometric assessments of Subjective Effects Questionnaire (Visual Analog Scales (VAS)) and 5-Dimensional Altered States of Consciousness ((5D-ASC), and wherein the MDMA enhances a positive over negative mood effect profile of the LSD in the individual; and
treating the psychiatric disorder that affects mood chosen from the group consisting of depression and anxiety.

* * * * *